US005481622A

United States Patent [19]
Gerhardt et al.

[11] Patent Number: 5,481,622
[45] Date of Patent: Jan. 2, 1996

[54] EYE TRACKING APPARATUS AND METHOD EMPLOYING GRAYSCALE THRESHOLD VALUES

[75] Inventors: Lester A. Gerhardt, Clifton Park, N.Y.; Ross M. Sabolcik, Austin, Tex.

[73] Assignee: Rensselaer Polytechnic Institute, Troy, N.Y.

[21] Appl. No.: 204,008

[22] Filed: Mar. 1, 1994

[51] Int. Cl.⁶ ..................................................... G06K 9/00
[52] U.S. Cl. .......................... 382/103; 382/171; 382/291; 345/158; 364/709.11
[58] Field of Search ............................. 382/1, 9, 48, 100, 382/103, 117, 171, 173, 291; 348/78; 345/8, 157, 158; 364/709.1, 709.11; 351/206, 209, 210, 245

[56] References Cited

U.S. PATENT DOCUMENTS

| | | | |
|---|---|---|---|
| 3,236,578 | 2/1966 | Mackworth et al. | 351/7 |
| 3,542,457 | 11/1970 | Balding et al. | 351/7 |
| 4,102,564 | 7/1978 | Michael | 351/7 |
| 4,595,990 | 6/1986 | Garwin et al. | 364/518 |
| 4,625,329 | 11/1986 | Ishikawa et al. | 382/1 |
| 4,648,052 | 3/1987 | Friedman et al. | 364/550 |
| 4,748,502 | 5/1988 | Friedman et al. | 358/93 |
| 4,815,839 | 3/1989 | Waldorf | 351/210 |
| 4,836,670 | 6/1989 | Hutchinson | 351/210 |
| 4,852,988 | 8/1989 | Velez et al. | 351/210 |
| 4,988,183 | 1/1991 | Kasahara et al. | 351/210 |
| 5,002,385 | 3/1991 | Kasahara et al. | 351/210 |

(List continued on next page.)

FOREIGN PATENT DOCUMENTS

| | | | |
|---|---|---|---|
| 0456166 | 11/1991 | European Pat. Off. | 351/209 |
| 1090333 | 5/1985 | U.S.S.R. | A61B 3/14 |

OTHER PUBLICATIONS

Cunningham, R., "Segmenting Binary Images", Robotic Age, Jul./Aug. 1981, pp. 4–19.
Kitter, J., Illingworth, J., & Föglein, J., "Threshold Selection Based on a Simple Image Statistic", Computer Vision, Graphics, and Image Processing, 1985, vol. 30, pp. 125–147.
Haralick, R. M. & Shapiro, L. G., "Survey: Image Segmentation Techniques", Computer Vision, Graphics and Image Processing, 1985, vol. 29, pp. 100–132.
"The Eyegaze Computer System", LC Technologies, Inc., Product Brochure, Aug. 1991, (13 pages).
Haralick, R. M., Sternberg, S. R. & Zhuang, X., "Image Analysis Using Mathematical Morphology", IEEE Transactions on Pattern Analysis and Machine Intelligence, vol. PAMI-9, No. 4, Jul. 1987, pp. 532–550.

Primary Examiner—Leo H. Boudreau
Assistant Examiner—Andrew W. Johns
Attorney, Agent, or Firm—Heslin & Rothenberg

[57] ABSTRACT

An eye-tracking system determines the position of a user's pupil and maps this position into a point of regard of the user on an interface device, such as a display screen, or other real-world object by a system comprising a camera for acquiring a video image of the pupil; a frame grabber coupled to the camera for accepting and converting analog video data from the camera to digital pixel data; a computer coupled to the frame grabber for processing the digital pixel data to substantially determine the position of the pupil; a display screen coupled to the computer; and a support connected to the camera and display screen for fixing the relative physical positions thereof relative to the user's pupil. The processing performed by the computer may include the selection of a first pixel intensity threshold for the segmentation of the digital pixel data into first and second groups, where the total pixel area of the first group is selected to be substantially equal to a pre-determined value expected to correspond to the area of a user's pupil. The system may be calibrated by the user's following a cursor on the display screen while the system measures the pupil position for known locations of the cursor.

35 Claims, 16 Drawing Sheets

U.S. PATENT DOCUMENTS

| | | | |
|---|---|---|---|
| 5,016,282 | 5/1991 | Tomono et al. | 382/2 |
| 5,034,618 | 7/1991 | Akeel et al. | 250/561 |
| 5,049,147 | 9/1991 | Danon | 606/10 |
| 5,070,883 | 12/1991 | Kasahara | 128/745 |
| 5,093,567 | 3/1992 | Staveley | 250/221 |
| 5,094,521 | 3/1992 | Jolson et al. | 351/210 |
| 5,109,425 | 4/1992 | Lawton | 382/1 |
| 5,189,512 | 2/1993 | Cameron et al. | 358/93 |
| 5,325,133 | 6/1994 | Adachi | 351/209 |

EYE IMAGE
($X_{eye}$, $Y_{eye}$)

IMAGE TO SCREEN MAPPING

DISPLAY SCREEN
($X_{screen}$, $Y_{screen}$)

EYE TRACKING APPARATUS AND METHOD EMPLOYING GRAYSCALE THRESHOLD VALUES

FIELD OF THE INVENTION

The present invention relates generally to a vision-tracking system and more particularly to an eye-tracking system that uses digital processing of an image of an eye to locate the eye's viewing direction.

DESCRIPTION OF THE PRIOR ART

Often there is a need to interact with a computer without the use of one's hands. This need may arise because one's hands are occupied while executing some task or as the result of a physical disability which prevents one from having sufficient physical control over one's hands to manipulate a traditional input device such as a keyboard. Interaction with a computer through the use of one's eyes is one way to satisfy this need. For example, where a person is afflicted with severe physical disabilities, eye movements can represent one of the few remaining motions that can be readily controlled. A physically-disabled person could interact with the computer through a system able to track and respond to the motion of one or both of his eyes.

Several prior eye-tracking systems have been built to track the motion of the eye in its viewing of objects. Earlier systems determined the eye's motion directly by physical contact with the eye, while current systems determine its motion indirectly by sensing light reflected from the eye's surface. Applications of prior eye-tracking systems have included the determination of the parts of advertising that catch a viewer's attention, and the evaluation of the layout of automotive dashboards and cockpit displays to determine their effectiveness for drivers and pilots.

Some recent eye-tracking systems have permitted a user to use the eye as a control input to a computer. In one example of such an application, a user selects words from a menu on a video screen to produce synthesized speech. This system operates by determining the intersection of the eye's line of sight with the plane of the screen to determine a so-called "point of regard", which is the point which the user is looking at on the screen and corresponds in this case to a menu selection. In other applications, however, the eye's point of regard generally corresponds to the physical point at which the eye is looking, whether on a display screen or elsewhere in three-dimensional space. The location of the point of regard is determined by the eye-tracking system and used as a control input for interactive control by the user.

Although certain prior systems permit a user to have some interactive control of a computer, these systems exhibit several disadvantages. In determining the eye's point of regard it is necessary to know the relative positions of the sensing camera, the display screen, and the user's eye. One of the more recent interactive systems fixes the position of the display screen and the sensing camera relative to one another, but not relative to the user. Thus, the user's physical position must be restrained for proper functioning. This is a disadvantage because the user's head must remain stationary for long periods of time leading to increased fatigue.

Another interactive system places the sensing camera on a helmet worn by the user. Although the camera's position relative to the user is fixed, the display screen's relative position is not. Instead, the display screen is mounted in a fixed position apart from the helmet. Therefore, an additional helmet sensor is required to track the position and orientation of the head. As a result, in this system the positions of the head and the eye must both be calculated to determine a point of regard. This second calculation for the head position increases the computational requirements of the system. In addition, both this and the aforementioned systems suffer from large physical size, lack of portability, and excessive cost.

Thus, there is a need for an eye-tracking system that will not restrict the mobility of the user, is portable, is more affordable, and avoids the additional computational overhead associated with tracking the relative positions of system components (or of the user), other than that of the eye itself.

SUMMARY OF THE INVENTION

This need is satisfied, the limitations of the prior art overcome, and other benefits realized in accordance with the principles of the present invention by a vision-tracking system for determining a point of regard. In one approach, the vision-tracking system determines the point of regard by determining the position of a pupil of a first vision means by digital image processing and then relating this position to a point of regard in the real-world of the first or a second vision means (e.g. the point of regard on a display screen or on a selected object in three-dimensional space). Although the pupil position being determined is that of a first vision means, the point of regard being determined can be that of either the first or the second vision means. The point of regard may be that of the second vision means in situations where the pupil position of the first vision means substantially corresponds to the point of regard of the second vision means. This situation occurs, for example, in a typical pair of human eyes in which the left eye's pupil position closely tracks the right eye's pupil position.

In one aspect of the present invention, the vision-tracking system comprises:

a camera means for acquiring a video image of a vision means, wherein the video image comprises a pupil image;

a frame grabber means, coupled to the camera means, for accepting video data corresponding to the video image from the camera means and converting the video data to digital pixel data;

a computer means, coupled to the frame grabber means, for processing the digital pixel data to substantially determine the position of the pupil;

a feedback means, coupled to the computer means, for accepting feedback data corresponding to the pupil position from the computer means; and a support means, connected to the camera and feedback means, for fixing the relative physical positions of the camera and feedback means.

The processing performed by the computer means of the vision tracking system may further comprise the selection of a first pixel intensity threshold for the segmentation of the pixel data into first and second groups. This processing may also comprise the following steps:

grouping individual pixels from one of the first or second groups into a first set having at least one pixel blob (note: a blob is a region of connected pixels belonging to the same group); and selecting from the first set one of the pixel blobs corresponding to the pupil image.

The feedback means may be a display screen, and the processing by the computer means may further comprise determining the position of the pupil image in image coordinate space, and mapping the position of the pupil image in image coordinate space into a position in display screen coordinate space.

In another aspect of the present invention, the first pixel intensity threshold is selected so that the total pixel area of the first group is substantially equal to a pre-determined expected pupil area, and the step of selecting one of the pixel blobs corresponding to the pupil image comprises the steps of:

calculating one or more statistics for each of the pixel blobs;

comparing the statistic for each pixel blob with an expected value corresponding to the pupil image to calculate a difference error; and selecting the pixel blob corresponding to the pupil image where the difference error is less than a pre-determined tolerance.

In a further aspect of the present invention, the vision tracking system comprises at least one light source mounted on the support means that illuminates the vision means and creates a radiation intensity highlight on the vision means. In this aspect, the processing by the computer means may also comprise the steps of:

selecting a second pixel intensity threshold, greater in intensity than the first pixel intensity threshold, for the segmentation of the pixel data into third and fourth groups, the second pixel intensity threshold being selected so that the total pixel area of the fourth group is substantially equal to a predetermined expected area for all highlights of the light sources illuminating the vision means;

grouping individual pixels from the fourth group into a second set having at least one pixel blob;

selecting from the second set one of the pixel blobs corresponding to a first highlight; and comparing the relative positions of the pixel blob corresponding to the pupil image and the pixel blob corresponding to the first highlight to determine the point of regard of the vision means.

Yet another aspect of the present invention is realized in a digital vision-tracking system by a tracking method for determining a point of regard. This method comprises the steps of:

acquiring video data from a camera corresponding to a video image of a vision means having a pupil, wherein the position of the pupil corresponds to the point of regard and the video image comprises a pupil image;

converting the video data to digital pixel data corresponding to the video image using an analog-to-digital interface coupled to the camera;

processing the pixel data in a computer coupled to the analog-to-digital interface to substantially determine the position of the pupil by a processing method comprising the step of selecting a pixel intensity threshold for the segmentation of the pixel data into first and second groups; and providing feedback data corresponding to the pupil position.

The feedback data may be provided by a display screen, and the pixel intensity threshold may be selected so that the total pixel area of the first group is substantially equal to a pre-determined expected pupil area. The processing by the computer may also further comprise the steps of:

grouping pixels from the first group into a first set having at least one pixel blob;

selecting from the first set one of the pixel blobs as corresponding to the pupil image;

determining the position of the pupil image by a calculated value based on a property of the selected pixel blob; and mapping the position of the pupil image in image coordinate space into a position in display screen coordinate space.

An advantage of the present invention is that all system components may be carried on one's person, including a portable personal computer and a power supply in a small backpack. Other advantages include hands-free operation, reduced cost due to the elimination of head-position sensing, reduced computational complexity, and robust tolerance to head and body movements and variations in lighting. Further, in one embodiment both the camera and feedback means are directed to a single eye to reduce the error in eye-tracking. Alternatively, in a different embodiment the camera is used to sense the pupil of one eye while the other eye is free to view a monitor or the surrounding environment. The foregoing and other objects, features, and advantages of the invention will be apparent from the following more particular description of a preferred embodiment of the invention, as illustrated in the accompanying drawings.

BEST MODE FOR CARRYING OUT THE INVENTION

In the operation of a vision-tracking system there are two primary functions of interest: acquisition of position information about the pupil of a vision means, and determination of the point of regard of the vision means (or a corresponding second vision means) based on this position information. In one particular case, the vision means is a human eye and the point of regard is the object in the real world which the user is looking at. A specific system implementing these two primary functions is described below as one embodiment of a vision-tracking system according to the present invention. The physical structure of the system (also hereinafter referred to as an "eye-tracking system") is described first, and then the architecture and operation of the system are next described. Finally, modifications and other embodiments of the present invention are described.

Although the following description of the present invention discusses a system for use with a human eye, it is not intended that the present invention be limited as such. Instead, as will be recognized by one skilled in the art, the present invention may be used with other vision means, such as artificial or robotic viewing mechanisms or the eyes of animals. In general, such a vision means need only comprise a pupil having an external shape that can be captured in a video image and related to a point of regard by image processing according to the present invention.

Physical Structure

Figure 1:
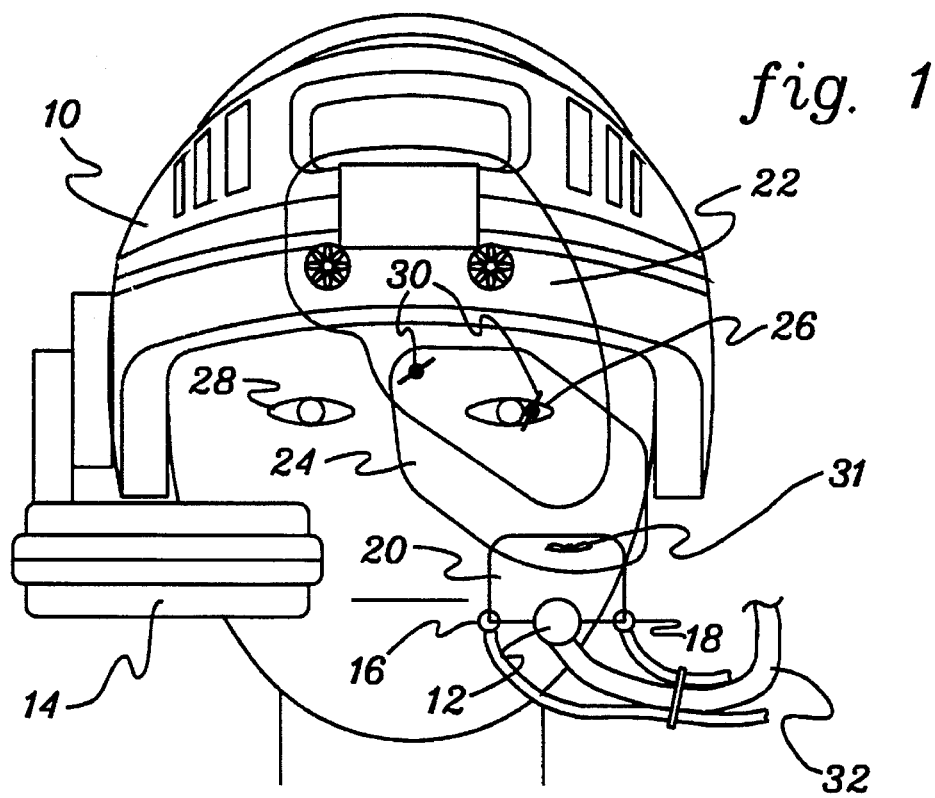
FIGS. 1 and 2 are front and side views, respectively, of the helmet-mounted components of one embodiment of a vision-tracking system according to the present invention.

First, the physical structure of one particular embodiment of an eye-tracking system is described. Referring to FIG. 1, a helmet 10 supports a video camera 12, a video display screen 14, and two LED light sources 16 and 18. Camera 12 and LEDs 16 and 18 are supported on a mounting block 20. Two plastic plates 22 and 24 connect mounting block 20 to helmet 10. Mounting block 20 is positioned relative to helmet 10 such that camera 12 and LEDs 16 and 18 are positioned substantially in front of a user's eye 26. Display screen 14, on the other hand, is positioned substantially in front of a second user's eye 28. Plate 22 is firmly mounted to helmet 10. However, plate 24 can be adjusted relative to plate 22 via wing nuts 30. Similarly, mounting block 20 can be adjusted relative to plate 24 via wing nut 31. A standard NTSC video cable 32 is connected to camera 12 for transmitting an analog video signal to the rest of the eye-tracking system.

Two power-supply cables (not shown) are connected to LEDs 16 and 18, and a standard video display cable (not shown) is connected to display screen 14. LEDs 16 and 18 are preferably infrared LEDs, and helmet 10 preferably fits firmly to the user's head and substantially prevents any motion of camera 12 and display screen 14 relative to eyes 26 and 28. Relative motion of these components will result in errors in the mapping of the pupil position of eye 26 into a position on display screen 14. A preferred example of helmet 10 is a hockey helmet, but other helmets such as hats, goggles, headbands, or masks may be used in other embodiments.

Although in this particular application camera 12 and display screen 14 are mounted in front of separate eyes, in other applications these components are preferably directed to a single eye so that the other eye is free to view the surrounding scene or other real-world objects. Directing both the camera and the display screen to the same eye is also advantageous in situations where the user has a physical impairment (such as in a handicapped person) that prevents one eye from repeatably tracking the other eye. The eye-tracking system as described herein can be used with such a system directed to a single eye, as can be recognized by one of skill in the art.

For example, a preferred alternative embodiment for the physical structure of the eye-tracking system has a camera mounted on the side of the helmet (or on the side of a sturdy pair of glasses) looking at the eye through a prism mounted appropriately on the helmet. A display screen is mounted on top of the helmet (or on top of the glasses) and projects its image onto, say, a half-silvered mirror surface. This mirrored surface is a part of the prism through which the camera looks and permits the use of the same eye for both the camera and the display screen. Such a system provides greater eye-tracking accuracy, improved field of view, and reduced eye strain.

Also, in other embodiments it is preferred that the camera and LEDs not be mounted directly in front of the user's eye so that the user's view of the real world is not obscured and so that the torque produced on the helmet by the weight of these components is reduced. Sometimes, excessive torque results in neck strain, particularly for physically-handicapped users.

Referring again to FIG. 1, display 14 may be, for example, the PC Private Eye display manufactured by Reflection Technology of Waltham, Mass. The Private Eye is a small (3 cm×3.3 cm×8.9 cm), light-weight (106 g) screen which produces a 30.5 cm virtual image at a distance of 61 cm. Also, the Private Eye is a PC-compatible display which can be operated as a monochrome CGA video adapter. The small size and light weight of the Private Eye make it suitable for use as display screen 14. However, in other embodiments display screen 14 may be a color display and/or may be directed to more than one eye.

Plates 22 and 24 are manufactured of a translucent plastic so that the user may see through these plates into the surrounding world. Plates 22 and 24 are used here to permit the adjustment of the camera and LEDs relative to the user's eye. However, in other embodiments different means could be used to permit this adjustment.

Figure 2:
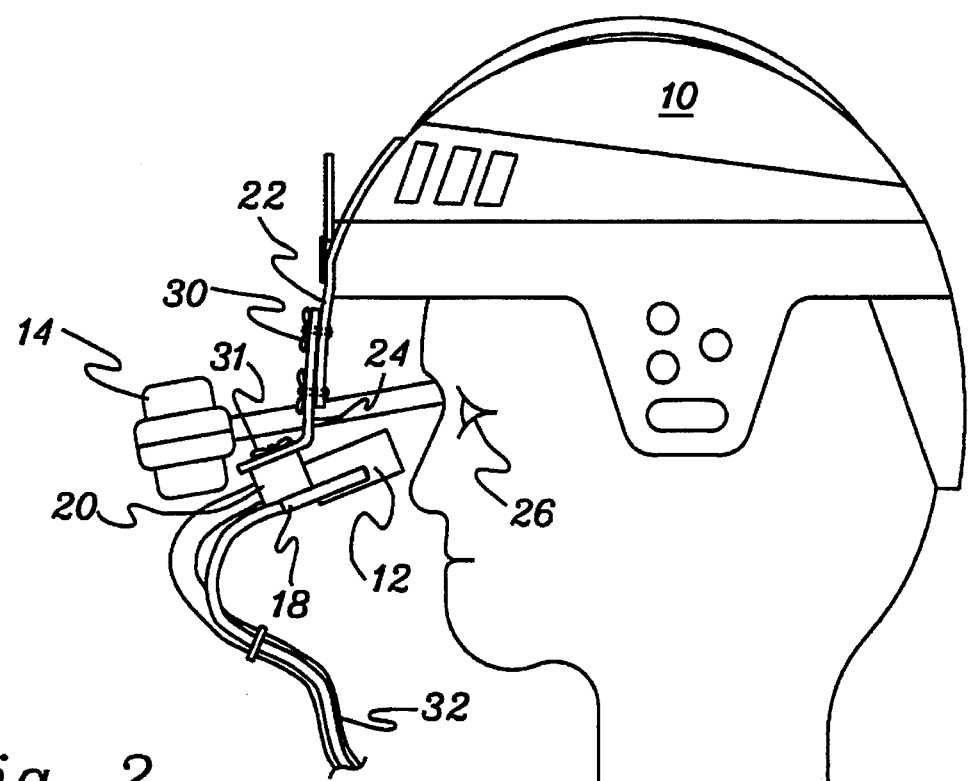

Referring now to FIG. 2, a side view of helmet 10 and its mounted components is shown. Video camera 12 is pointed so that eye 26 falls within its field of view, and LED 16 (not shown in FIG. 2) and LED 18 are pointed so that eye 26 is evenly illuminated. Display screen 14 is positioned for ready viewing by eye 28 (not shown in FIG. 2). The position of plate 24 relative to plate 22 can be adjusted via wingnuts 30 as described above to adjust the aim of camera 12 and LEDs 16 and 18.

Although two LEDs are shown in FIGS. 1 and 2, depending upon the particular embodiment selected for use, the eye-tracking system will work with only a single LED or other light source. Two LEDs are preferred so that eye 26 is evenly illuminated. In other embodiments even more than two LEDs may be used, depending upon illumination requirements. Also, because helmet 10 mounts both camera 12 and display screen 14 in a fixed position relative to eyes 26 and 28, there is no need to track the location of the user's head in space. This is advantageous because it eliminates costly computational overhead associated with either head sensing or additional image processing.

Camera 12 may be either a black and white camera or a color camera. A black and white camera is advantageous for reducing image processing complexity in some applications. However, in other embodiments of the present invention a color video camera may be used depending upon speed requirements. Also, in other embodiments of the present invention, a light source(s) other than an LED may be used.

In general it is sufficient that the light source provide even illumination of the eye to be imaged by camera 12. Too little illumination will result in a compression of the image gray scale, failing to take advantage of the full dynamic range of camera 12. On the other hand, too much illumination will cause the imaging element of camera 12 to become saturated, which will result in a compression of the gray scale at the higher intensity range. Also, using ambient light may not be acceptable in some situations due to its often changing and poor illuminating qualities. It is preferred that a constant light source be used to ensure consistently good image data. Even illumination is advantageous to avoid any shadows which might be mistaken for the pupil of the eye. Light sources which may be used depending upon the application include incandescent lights, lighting through fiber optic cables, visible-light LEDs, and infrared-light LEDs. However, because charge-coupled-device video cameras are extremely sensitive to infrared illumination, it is preferred that infrared LEDs be used as the light source. Infrared LEDs are also valuable because IR light is not visible to the user.

One consideration in selecting IR LEDs is that thermal damage to the human tissue of the eye needs to be avoided. An accepted limit for exposure to IR laser sources for a period exceeding 10 seconds is about 100 mW/cm$^2$. The IR LEDs used should be less than this limit, for example, about 3.4 mW/cm$^2$. Another consideration which affects the number of LEDs required to evenly illuminate the entire eye is the cone angle of light emittance from the LED. For example, an IR LED may have a 20° cone at a wavelength of 880 nm, and given this particular cone angle along with the positioning of the LEDs relative to the eye as shown in FIGS. 1 and 2, two LEDs are preferably used.

System Architecture

Figure 3:
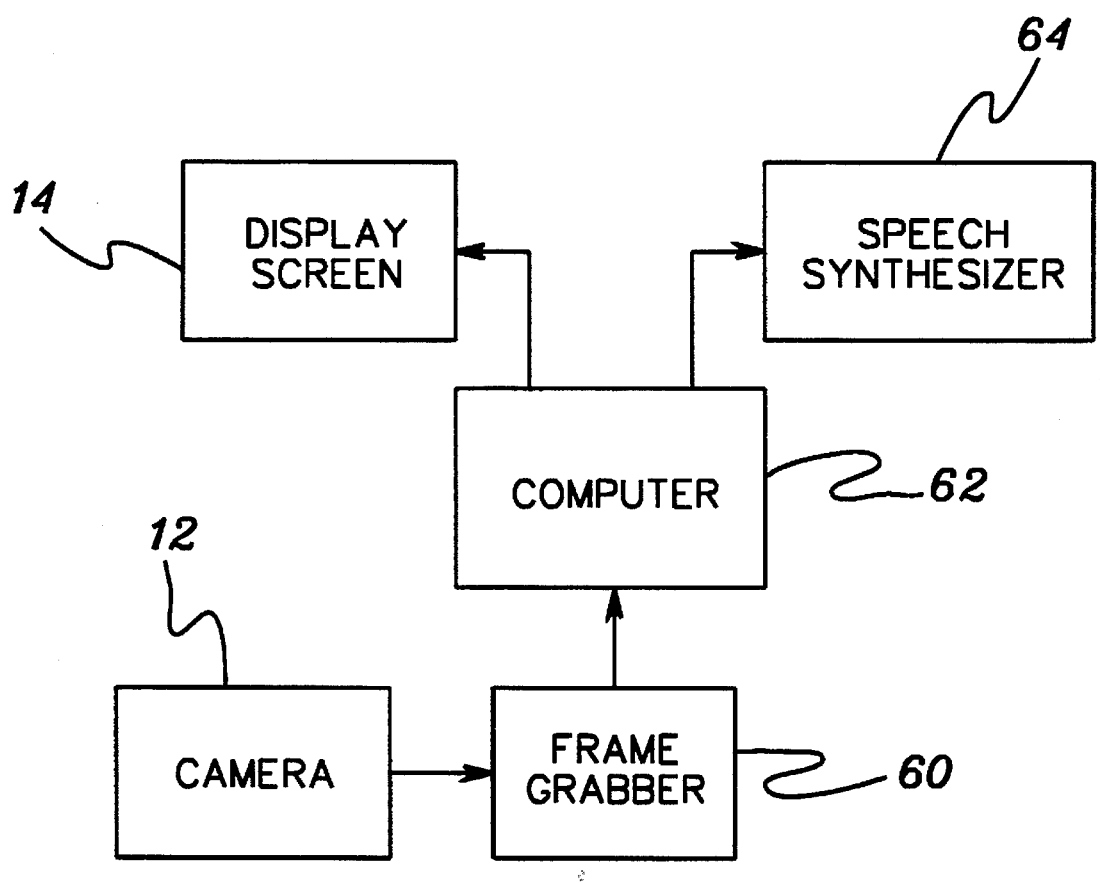
FIG. 3 is a system architecture block diagram for one embodiment of the vision-tracking system of the present invention.

FIG. 3 is a system architecture block diagram for one embodiment of the eye-tracking system according to the present invention. Camera 12 provides an analog video output to a frame grabber 60, which converts the analog video data to digital pixel data corresponding to the current image frame acquired by frame grabber 60 from camera 12. The digital pixel data output of frame grabber 60 is transmitted to a computer 62 for processing the pixel data to substantially determine the position of the user's pupil.

In general, frame grabber 60 is a frame grabber card capable of converting a composite video signal into a digital image such as, for example, a 640×480 7-byte gray scale pixel image. An example of a frame grabber card that may be used is a VIDEO PIX frame grabber card which resides in a SUN MICROSYSTEMS SPARCstation2. However, in other applications, frame grabber 60 could be any device capable of converting a video signal into a digital image.

Display screen 14 is connected to an output of computer 62 by a standard video interface and cable, and (in an example of one specific application of the eye-tracking system) a speech synthesizer 64 is connected to a second output of computer 62. Other output applications could be additionally connected to computer 62 as recognized by one skilled in the art.

Computer 62 is a general purpose microcomputer, such as a SUN SPARCstation or any of a number of PC-compatible computers (e.g. a conventional, portable 50 MHz Intel 486 PC computer having a docking station with ISA slots to accommodate a frame grabber and a video display). Computer 62 is responsible for handling several different processing tasks which support the eye tracking system's operation. These tasks include digital image processing, generation of the user interface screens, and handling of communication between these and other tasks running on computer 62.

It should be noted that although a general purpose computer and discrete frame grabber are described above, one skilled in the art will recognize that an application specific integrated circuit (ASIC), or dedicated configurations of discrete components, could alternatively be used to implement some (or all) of the functions of the general purpose computer, the frame grabber, or other components of the eye-tracking system according to the present invention. The present invention is intended to encompass all such modifications as falling within the scope of the appended claims.

In one specific application of the eye-tracking system according to the present invention, a user is able to select a string of words for speech synthesis by gazing at each word on display screen 14 for a set period of time. By consecutively gazing at several locations, several words can be chained together into sentences which can then be sent to speech synthesizer 64 to vocalize the words. Speech synthesizer 64 may be, for example, handled by an AM79C30 Digital Controller chip built into a SUN SPARCstation.

The image processing task on computer 62 handles several functions related to the processing of the video image of the user's eye. These responsibilities include locating the pupil, mapping the pupil coordinates to display screen coordinates, and informing peripheral devices of the pupil location. In addition these functions, the image processing task may also provide an additional interface (in addition to display screen 14) for overall control of the system by the user or another person. This interface would allow this person to view a gray scale or thresholded version of the digital pixel image of the user's eye, to calibrate the system, or to run certain aspects of the system.

The image processing task resides on computer 62 inside a continuous loop, which involves continually acquiring an eye image with camera 12 and attempting to locate the pupil position. If the pupil is found, its location is then mapped from camera image coordinates to display screen coordinates, which are then sent to the user interface task. The image processing task is discussed in greater detail below in the section so titled.

A primary function of display screen 14 is to act as a user interface for presenting information and feedback to the user of the eye-tracking system. At a fundamental level, this user interface (i.e. the display screen) provides information about the position of the user's pupil. This position may be represented on the user interface, for example, by a cursor. However, in more complicated applications such as the speech synthesis application above, the user interface may present a grid of squares to the user, which may be preprogrammed to display either characters or icons. When a user selects one of these squares, the square is highlighted to provide feedback, and an action is selected corresponding to the character or icon in that particular square. For example, each square may represent one of several actions: a link to another screen, a command message, or a special system control function. The action of linking to another screen permits menus to be chained together in order of increasing detail until a choice is made at the lowest-level screen in the chain. Examples of command messages that could be used include the following: pausing the system, calibrating the system, or exiting from the system.

Image Processing

Broadly speaking, after acquiring an analog image with camera 12, the eye-tracking system converts the image to a digital pixel representation of the image, determines a pixel intensity threshold and segments the pixel image into dark and light pixel groups (hereinafter referred to as "image thresholding"), groups segmented pixels of the same intensity (i.e. dark or light) into pixel blobs (in a preferred approach, a blob is simply a set of contiguous pixels), and selects one of these blobs as corresponding to the user's pupil. One reason for performing image thresholding is to simplify the data corresponding to the eye image. For example, reducing the data from a 7-bit greyscale image to a 1-bit binary image significantly reduces the computational requirements for processing the data.

The eye-tracking system determines a user's point of regard by determining the location of the pupil blob's centroid relative a reference corner of the image, arbitrarily designated as having say a coordinate position of (0,0), or relative to the position of a radiation highlight created by a light-emitting diode illuminating the surface of the eye. As mentioned above, the pupil's centroid position will have been previously calibrated for mapping into a display screen position. These image processing procedures are discussed in greater detail below.

Figure 4:
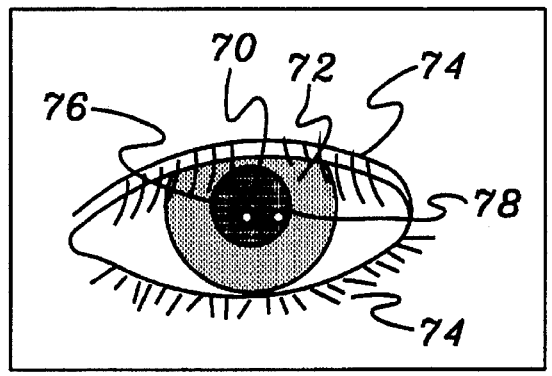
FIG. 4 is a typical eye image as captured by a video camera in a vision-tracking system using two LED light sources.

Referring to FIG. 4, a typical digital pixel image of the user's eye as it appears following acquisition by camera 12 and digitization by frame grabber 60 is illustrated. A pupil 70 is disposed in an iris 72, and eyelashes 74 are disposed above and below pupil 70. Two radiation intensity highlights 76 and 78 created by LEDs 16 and 18 (from FIG. 1) appear as light, substantially-circular regions within the darker region of pupil 70.

Figure 5:
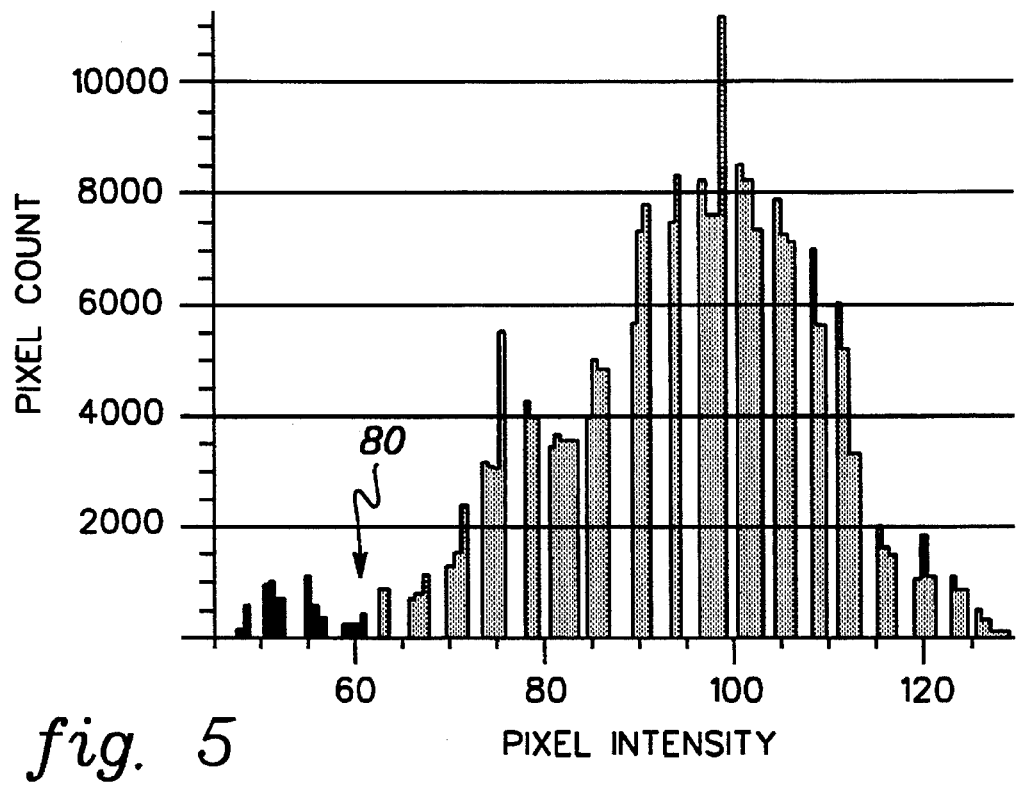
FIG. 5 is a histogram classified by the number of pixels per class for the captured eye image of FIG. 4.

FIG. 5 illustrates a histogram with several bins of pixel intensity data corresponding to the image of FIG. 4. More specifically, the vertical axis indicates the pixel count of each bin, and the horizontal axis indicates the magnitude of the pixel intensity of each bin. As this particular image is represented by a 7-bit greyscale, the data in this histogram is divided, for example, into 128 bins (numbered 0–127) each having a magnitude corresponding to the decimal integer value of the 7-bit pixel intensity.

According to the present invention, a pixel intensity threshold is selected to divide the image pixel data into two sets, a dark set and a light set. This threshold is selected so that the pixel data in the first set has a total pixel area substantially equal to a pre-determined, expected size of a user's pupil. For example, in FIG. 5 this threshold is a pixel intensity of about 61 (the segmented dark set here corresponds to the darkest five percent of the eye image and thus an area criterion of 5% is being used). The pixel bins below this threshold (these bins are indicated by arrow 80) correspond to the darkest pixels in the image of the user's eye, and the total area of these darkest pixels substantially equals the total area of pupil 70.

An area criterion is used in the present invention because it provides an adaptive thresholding technique that is robust and handles a wide range of dark and bright lighting conditions in a computationally efficient manner. The use of this criterion permits the threshold level to be changed for each image frame to adjust for changes in lighting conditions. Another reason for the use of an area criterion is that typical histograms for the eye image do not exhibit identifiable modes, and thus prior threshold selection techniques that rely upon bimodal assumptions for segmenting image data are not adequate here.

Figure 6:
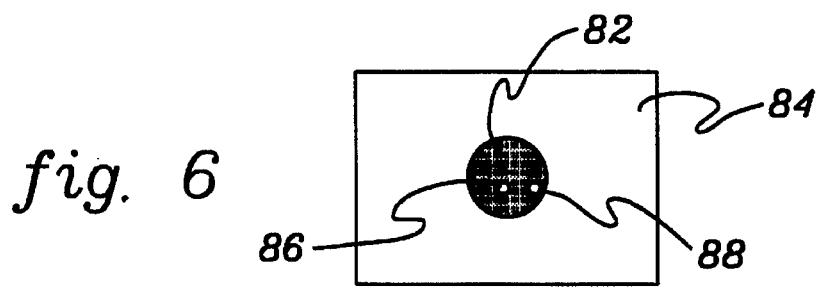
FIG. 6 is a thresholded binary image of the eye image of FIG. 4.

FIG. 6 illustrates a binary image following segmentation of pixels into light and dark sets based on the selected pixel intensity threshold from FIG. 5 above. A dark, substantially-circular region 82 substantially corresponds to pupil 70 of FIG. 4, and a lighter, background region 84 substantially corresponds to the remaining pixels of the eye image. The dark region (i.e. the pixel bins below the threshold) of the histogram in FIG. 5 represents the darkest 5 percent of the image shown in FIG. 4, and the binary image of FIG. 6 is the image resulting from this 5 percent threshold. The lighter, circular regions 86 and 88 correspond respectively to intensity highlights 76 and 78 of FIG. 4.

In other embodiments an area criterion lesser or greater than five percent may be used as will be recognized by one of skill in the art. However, as the area criterion is decreased, a decreasing number of pixels will be classified as being dark. The result of this may be an insufficient number of contiguous dark pixels necessary to define a pupil blob which will meet the criteria later used to select the pupil blob. This may occur, for example, because the pupil image is fragmented into smaller dark regions by regions of pixels defined as being light. On the other hand, as the area criterion is increased, a increasing number of pixels will be classified as being dark. This may result in the merging of non-pupil dark pixel regions into the pupil's dark pixel region. If this occurs, the pupil blob again might not be identified for failure to meet the chosen pupil blob selection criterion.

FIGS. 7a–7c and 8a–8c illustrate eye images, and their corresponding histograms and segmented binary images, for brighter and darker lighting conditions, respectively, of the user's eye than for the histogram shown in FIG. 5. First, in FIG. 7b the average pixel intensity is brighter relative to that of FIG. 5, as seen in the histogram, but the pupil area threshold criteria (note: the pixel intensity threshold here is about 75) still results in a properly segmented binary image. Second, looking now at FIG. 8b, although the average pixel intensity here is darker than that of FIG. 5, the same pupil area threshold criteria (note: the pixel intensity threshold here is about 35) also results in a properly segmented binary image. It should be noted that the same five percent area criterion is used in both FIGS. 7b and 8b.

Because the intensity threshold is selected based on a pixel area criterion, the image histogram pixels may shift either right (for brighter images) or left (for darker images) without substantially adversely affecting the successful selection of the threshold value. However, in the case of very extreme shifts, the method will fail due to compression of the histogram. This occurs because there is not enough dynamic range in the image to discriminate between regions. In other words, the pixels for the entire image will fall into only a few bins at one end of the image histogram making it impossible to successfully divide the pixel data into two meaningful sets.

Figure 7A:
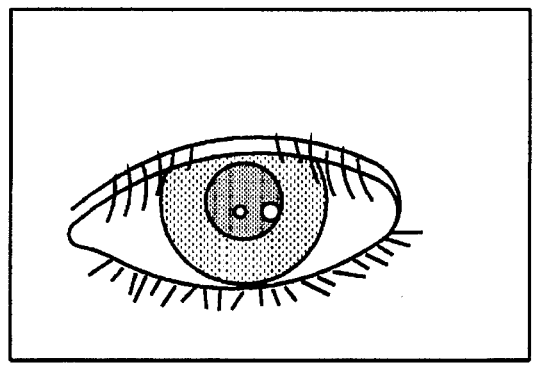
FIGS. 7a–7c are an image of an eye, a pixel histogram, and a thresholded binary image corresponding thereto, for lighting conditions having a greater intensity than that for FIGS. 4–6.
Figure 7B:
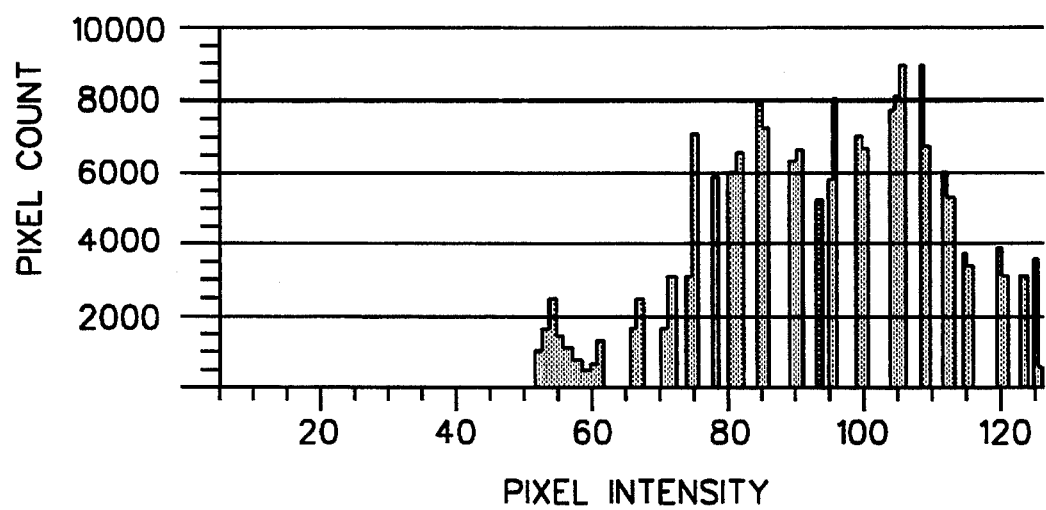
Figure 7C:
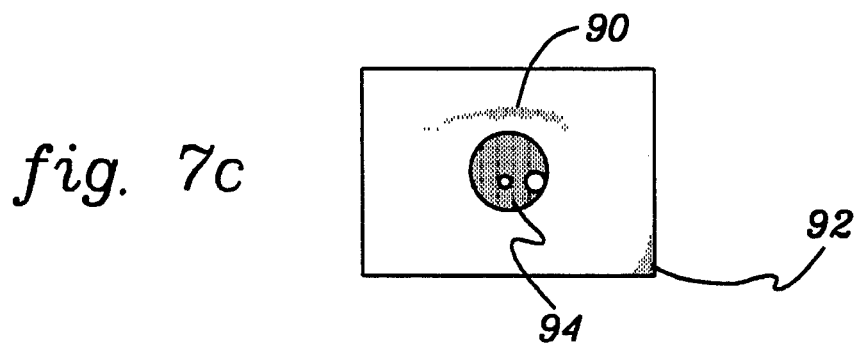
Figure 8A:
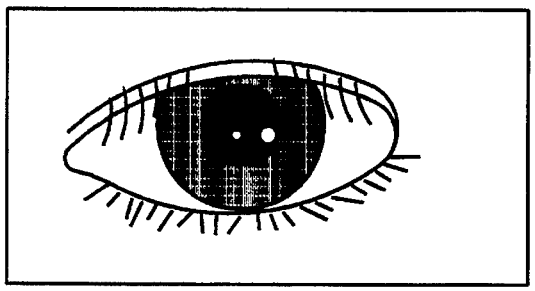
FIGS. 8a–8c are an eye image, a corresponding pixel histogram, and a thresholded binary image, for lighting conditions having an intensity less than that for FIGS. 4–6.
Figure 8B:
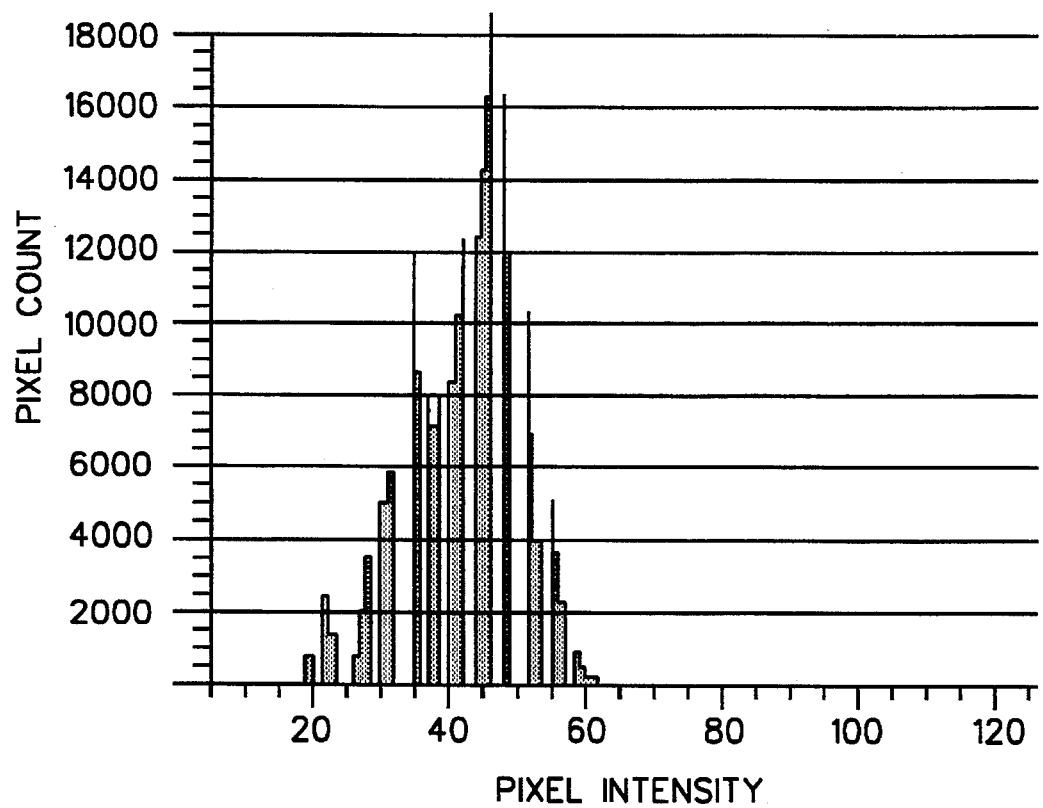
Figure 8C:
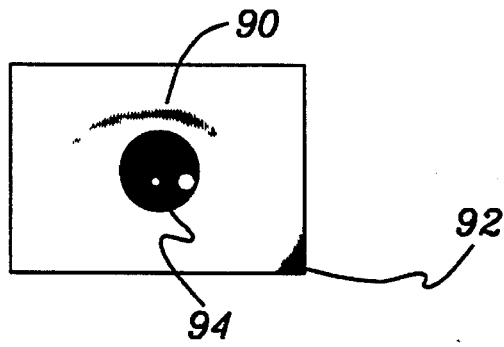

It should be appreciated that the two segmented binary images of FIGS. 7c and 8c further include dark regions corresponding to certain non-pupil elements that unavoidably appear in the eye image. For example, in FIGS. 7c and 8c dark regions 90 correspond to the user's eyelashes, and dark regions 92 correspond to portions of the user's eye not fully illuminated by LEDs 16 and 18 of FIG. 1. The present invention distinguishes these non-pupil elements from the pupil itself as described herein.

After segmenting the digital pixel image into dark and light pixel sets based on a pixel intensity threshold, one of typically several dark regions in the segmented binary image must be selected as corresponding to the user's pupil. The ultimate goal of this selection is to determine the center of the user's pupil and the user's point of regard. Generally, this selection involves defining sets of contiguous, dark pixels (these sets are referred to herein as pixel blobs or simply blobs) that correspond to the dark regions of the binary image. These pixel blobs are defined by clustering dark pixels based on some connectivity criteria (e.g. the proximity of one pixel to another). Next, certain properties are calculated for each pixel blob that are then compared with the properties expected for a pixel blob corresponding to the user's pupil. The pixel blob having properties most closely related to those expected for a pupil is selected as the so-called pupil blob. Referring to FIGS. 7c or 8c for example, in a successful selection one of dark regions 94 will be selected as corresponding to the user's pupil, rather than the selection of one of dark regions 90 or 92. After the pupil blob (e.g. one of dark regions 94) has been selected, the center position of the pupil blob is used to determine the user's point of regard, as discussed later below.

Now, discussing selection of the pupil blob in greater detail, in order to calculate properties for each of the dark regions in the binary eye image, it is first necessary to explicitly define each of the dark regions. This is done by assigning each dark pixel in the binary image (recall that each dark pixel is below the intensity threshold, as discussed above) to one of several contiguous sets of dark pixels. Each of these contiguous sets is called a blob. Assigning the dark pixels to blobs is a process known as binary image segmentation. An article titled *Segmenting Binary Images,* by Robert Cunningham, in Robotics Age, July/August 1981, pp. 4–19, describes segmentation approaches that may be adapted for use with the present invention and is hereby incorporated by reference in full.

In general, binary segmentation is based on measured properties of the pixels such as intensity or RGB color information and/or calculated properties like gradient magnitude and direction. In one preferred approach, binary segmentation is performed based on a binary pixel intensity designation of either dark or light, such as results from the image thresholding described above. Pixels in the eye image that are contiguous and both either dark or light are grouped together into the same blob. This use of a simple property distinction such as dark or light is advantageous in some cases for minimizing the number of required calculations and in turn increasing the speed of operation of the eye-tracking system.

In a preferred approach, pixel blobs are defined by a single-pass method that scans the binary pixel image from top-to-bottom and left-to-right. When each new pixel is examined during the scan, it is determined whether the pixel is connected to another pixel of the same color (i.e. dark or light). This preferred approach implements a so-called single-linkage, region growing technique which starts with a single pixel (which is analogous to a seed, hence the name "region-growing") and grows the boundary of the region by adding similar pixels to the region.

Figure 9:
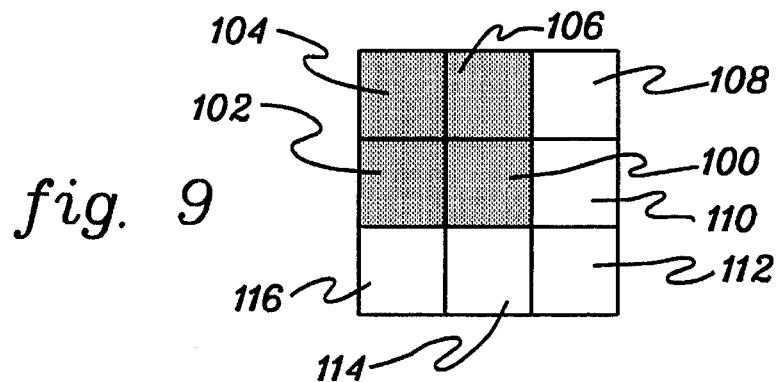
FIG. 9 illustrates the pixels examined for connectivity during the scanning of an eye image during blob formation.

Referring to FIG. 9, according to a region-growing approach, a current pixel 100 is being examined. To minimize processing, only three pixels (pixels 102, 104, and 106) of a total eight adjacent pixels are checked for connectivity to current pixel 100. Pixels 108, 110, 112, 114, and 116, however, are not checked with respect to current pixel 100.

In the general case each of pixels 102, 104, and 106 will each be associated with a blob defined earlier in the scanning of the eye image. Current pixel 100 will be added to one of a maximum of three possible blobs associated with pixels 102, 104, and 106 depending upon whether current pixel 100 is of the same intensity as one of pixels 102, 104, and 106. For example, if both current pixel 100 and pixel 104 are dark, then pixel 100 is added to a linked-list defining a blob of which pixel 104 was typically made a member of earlier in the scan. Also, if pixel 100 is the same color as pixels 102 and/or 106, it is added to the linked-list corresponding to pixels 102 and/or 106. Although three adjacent pixels are checked in this embodiment, in other embodiments the number of adjacent pixels and/or order of connectivity checking could be varied.

On the other hand, if current pixel 100 and pixel 104 are of different colors, then pixel 100 is not added to the blob set that includes pixel 104. However, later in the single-pass scan of the eye image when, for example, pixel 112 is the current pixel under examination, if pixel 100 and pixel 112 are of the same color, then a linked-list will be created (if not earlier created in another part of the image scan) to define a pixel blob that includes both pixels 100 and 112. Also, if pixel 100 is not the same color as pixels 102 and/or 106, then a new linked-list is created which only contains pixel 100.

Although a region-growing technique is described herein, one skilled in the art will recognize that other techniques could also be used to define the blobs. For example, a region-splitting technique could be used which starts with the entire eye image and then recursively divides the image into regions until all pixels within any given region are similar.

As a result of the above region-growing method, after the single-pass scan each pixel in the eye image is assigned to a pixel blob containing either all dark or all light pixels. Next, after defining blobs for the dark regions of the image, blob properties are determined for each blob and stored as a linked-list of blob descriptors along with the pixel definition of the corresponding blob formed during the scanning above. Examples of such blob descriptors include the pixel area of the blob (i.e. the number of pixels in the blob for pixels of a fixed size), the blob's centroid (i.e. the x and y coordinates of the blob's center of mass), and the x and y-coordinate maxima and minima for the pixels within the blob (these coordinates define the bounding rectangle for the blob). Specifically, the x-coordinate of the blob centroid is found by dividing the sum of the x-coordinates of all blob pixels by the total number of pixels within the blob. The y-coordinate of the centroid is found similarly.

Figure 10:
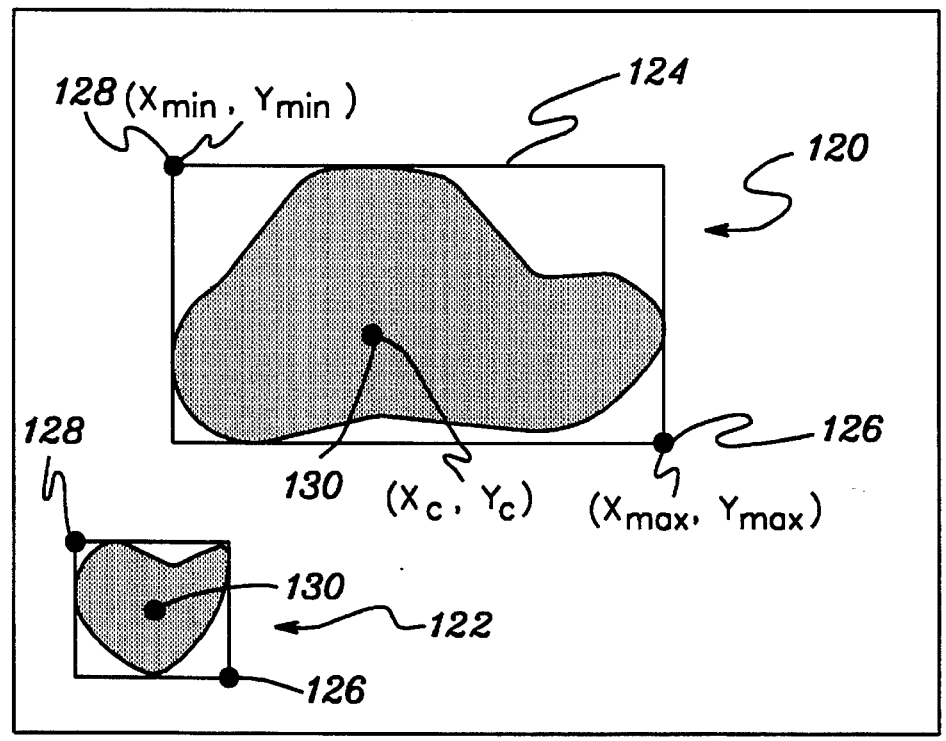
FIG. 10 illustrates a pair of pixel blobs, showing a centroid of one blob and the rectangular boundaries of both blobs.

FIG. 10 illustrates some preferred blob properties. Specifically, a first blob 120 and a second blob 122 are shown for a simplified case. Blob 120 has a bounding rectangle 124 therearound that corresponds to the x and y-coordinate maxima 126 and minima 128 for the pixels within blob 120. Also shown is a centroid 130 for each blob. Another useful blob property (not shown) is the length-to-width ratio of the bounding rectangle, which is defined as $(X_{max}-X_{min})/(Y_{max}-Y_{min})$ where $X_{max}$, $X_{min}$, $Y_{max}$, and $Y_{min}$ are the extrema of the blob's bounding rectangle. In other embodiments, other blob properties may also be used such as the perimeter of the blob or its moments of inertia, as will be recognized by one skilled in the art.

After defining the blobs for the eye image and determining properties for each blob, the next step according to the present invention is to select the blob corresponding to the user's pupil from other blobs that correspond to elements such as dark image shadows or dark eyebrows. This selection of the pupil blob is required because there is typically more than one blob due to other dark elements in the eye image.

Figure 11:
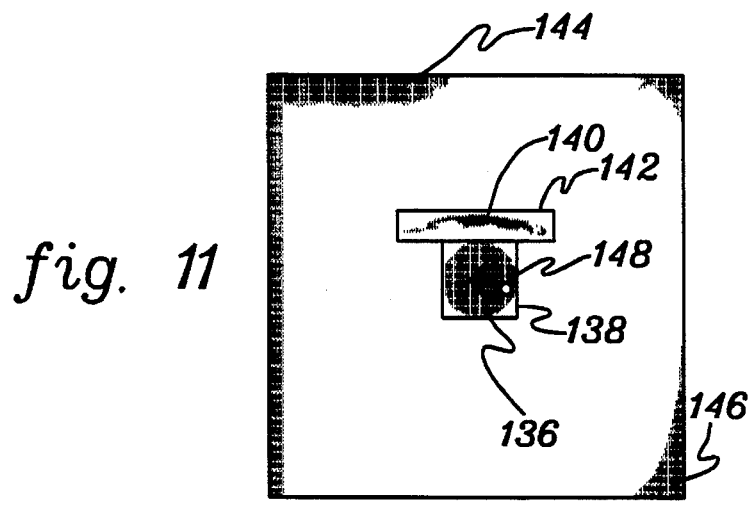
FIG. 11 illustrates a typical eye image following image thresholding and blob definition.

FIG. 11 is a typical image following blob definition in which more than one blob has been defined. Pupil blob 136 corresponds to the user's pupil and has a bounding rectangle 138, and blob 140 corresponds to the user's eyebrow and has a bounding rectangle 142. Further, blobs 144 and 146 correspond to image shadows created by the concentric lighting pattern from an IR LED light source. Blob 148 contains light pixels and corresponds to the radiation intensity highlight from an IR LED light source.

In general, pupil blob 136 is selected by comparing the each blob's properties to those pre-determined values that are expected for a blob corresponding to the pupil. In one embodiment, the properties used for selecting the pupil blob are area and length-to-width ratio (also referred to herein as eccentricity). Blobs that are smaller or larger than the pre-determined area are rejected as non-pupil blobs. Also, blobs that have an eccentricity ratio differing substantially from 1.0 are rejected as non-pupil blobs because it is expected that the user's pupil blob will typically be circular with a ratio of about 1.0.

Although the length-to-width ratio is used in this embodiment, a better measure of the circularity of a blob is found by using the second moment of inertia of the blob. Specifically, similar calculated moments of inertia about both the x and y axes would indicate symmetry about the blob's centroid and that the given blob is a pupil blob.

In the present embodiment, the pupil selection method according to the present invention, which is discussed in greater detail below, maintains running averages of both the area and eccentricity for pupil blobs selected in previous eye image frames. These averages aid in reducing the effects of atypical eye image frames and also result in an adaptation of the eye-tracking system to the characteristics of the current user's eye, which may differ somewhat from the pre-determined values initially used by the system at start-up.

Each blob in the eye image has its area and eccentricity compared to the running average values. The primary selection is based upon blob area, and the blob having an area closest in value to that of the running average pupil blob area is tentatively selected as corresponding to the pupil blob. After this tentative selection, if the blob's area and length-to-width ratio are within a pre-determined percentage tolerance, say 10%, of the respective running averages, then the blob is selected as being the pupil blob. Once this pupil blob selection is made, the running average area and eccentricity are updated with the values for the current pupil blob.

In some cases the pupil blob selection will fail. This may occur, for example, because the user blinks, in which case there is no pupil in the eye image, or the pupil itself changes due to a contraction or dilation, which changes the area of the pupil significantly relative to the running average pupil area. The present invention accommodates a failure in pupil blob selection by modifying the blob comparison tolerances after selection fails for a fixed number of eye image frames. Specifically, a miss counter is incremented for each selection failure and decremented for each successful pupil blob selection. Upper and lower limits are placed upon the value of the miss counter.

In a preferred approach, if the miss counter reaches the upper limit, then the percentage tolerance is relaxed from say 10% to 15%. With each additional failure the percentage tolerance is relaxed say an additional 5% up to a pre-determined maximum of say 30% (this pre-determined maximum is reached when the MISS counter is greater than or equal to a pre-determined maximum limit). If these relaxed tolerances result in a successful pupil blob selection, then the miss counter is decremented for each successful pupil blob selection. When the miss counter reaches the lower limit, say zero, (which typically is its original start-up value), each additional successful pupil blob selection tightens the percentage tolerance by say 5% increments until the initial, pre-failure percentage tolerance is reached, at which point no further tightening is done. An advantage of this adaptive tolerance method is that the user's pupil may be re-acquired, and the running averages will reflect values for the re-acquired pupil.

In the preferred embodiment, only the area tolerance is relaxed and the MISS counter only corresponds to failures of the pupil blob to meet the area criterion. In this embodiment, the length-to-width ratio tolerance is not relaxed because each blob is required to be substantially circular.

However, in other embodiments, the length-to-width ratio (i.e. eccentricity) could be relaxed instead of, or even in addition to, the area tolerance. Further, the system may be designed so that the decision of which tolerance to relax depends upon that tolerance causing the largest number of pupil blob selection failures. To assist in this decision, a separate failure counter may be maintained for each tolerance, and the one with the largest counter value at a specified time could be relaxed first. In other embodiments, however, a global failure counter could be incremented for each failure to select due to any of the selection criteria being used (e.g. eccentricity and area). A global counter would be useful in situations where the occurrence of a failure is relatively rare (e.g. due to good image data) and only minor adjustments to the tolerances are necessary to correct for these failures.

Figure 12:
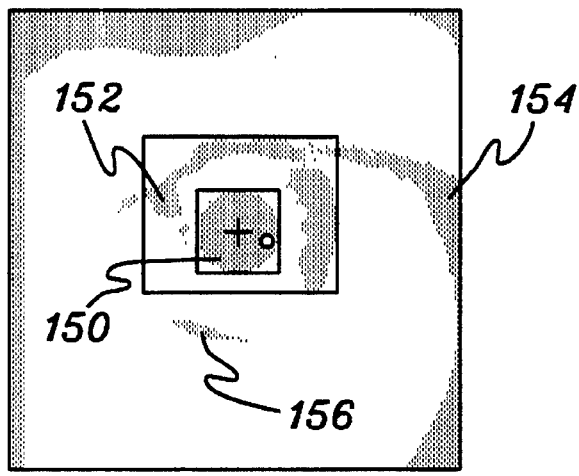
FIGS. 12–14 illustrate blob selection results for three different cases, including one case shown in FIG. 18 involving a blob selection failure.
Figure 13:
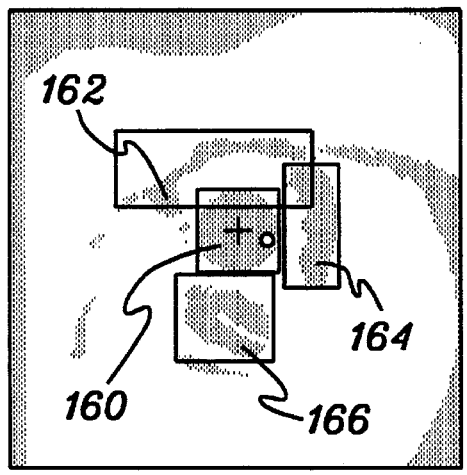

FIG. 12 illustrates an eye image having several defined blobs. Shown are a pupil blob 150 and other non-pupil blobs 152, 154, and 156. The pupil selection method according to the present invention is able to successfully select pupil blob 150 from the image of FIG. 12. FIG. 13 also illustrates an eye image having several defined blobs. Pupil blob 160 is shown with non-pupil blobs 162, 164, and 166. Again, the pupil selection method successfully selects pupil blob 160 (it should be noted that bounding rectangles are only shown for a few blobs for illustrative purposes).

Figure 14:
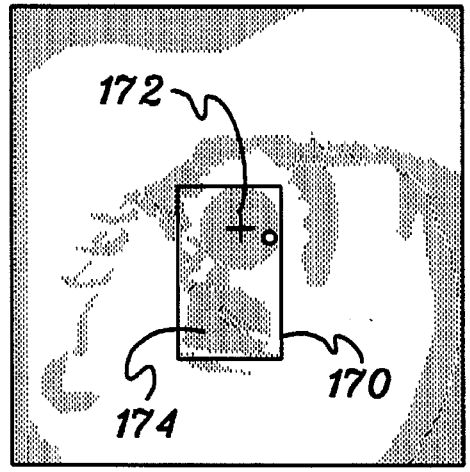

There are some cases, however, where the pupil selection method will fail to select a pupil blob. This occurs where none of a blob's features, such as area, are within the required tolerances, and FIG. 14 illustrates such a case. In FIG. 14 a blob 170 (as defined by a bounding rectangle) contains dark regions 172 and 174. Because dark region 174 links with dark region 172, which corresponds to the pupil, a separate blob has not been defined for dark region 172. Thus, no blob will have properties within the percentage tolerances necessary to be selected, and no blob is selected as the pupil blob for the image in FIG. 14.

More specifically, the selection failure occurs in FIG. 14 because the image threshold is too high, and the pixels outside of the pupil image fall below the threshold. This causes a linking of pupil pixels with certain non-pupil pixels that results in a non-complying blob. Other causes of a selection failure in other cases may include poor lighting, obstruction of the camera's field of view, movement of the display screen, shifting of the camera's relative position, and any extreme lighting changes.

One possible solution to the problem of non-pupil dark regions linking with the pupil dark region is to apply a morphological opening operator to the blob definition. This opening operator is applied to the binary image after image thresholding, but prior to blob building, and removes dark regions from the binary image that are smaller than a given width while leaving the remainder of the image unchanged. Following this morphological processing of the image, the blobs are formed as discussed above.

The use of an opening operator would be most valuable for extremely cluttered images with extensive linking between dark regions therein. A limitation on the use of such an opening operator, however, is that the operation is computationally intensive. Additional information on the use of morphological opening operators is discussed in an article titled *Image Analysis Using Mathematical Morphology*, by Robert M. Haralick et al., in IEEE Transactions on Pattern Analysis and Machine Intelligence, vol. PAMI-9, no. 4, July 1987, pp. 532–550, which is hereby incorporated by reference in full.

Figure 15:
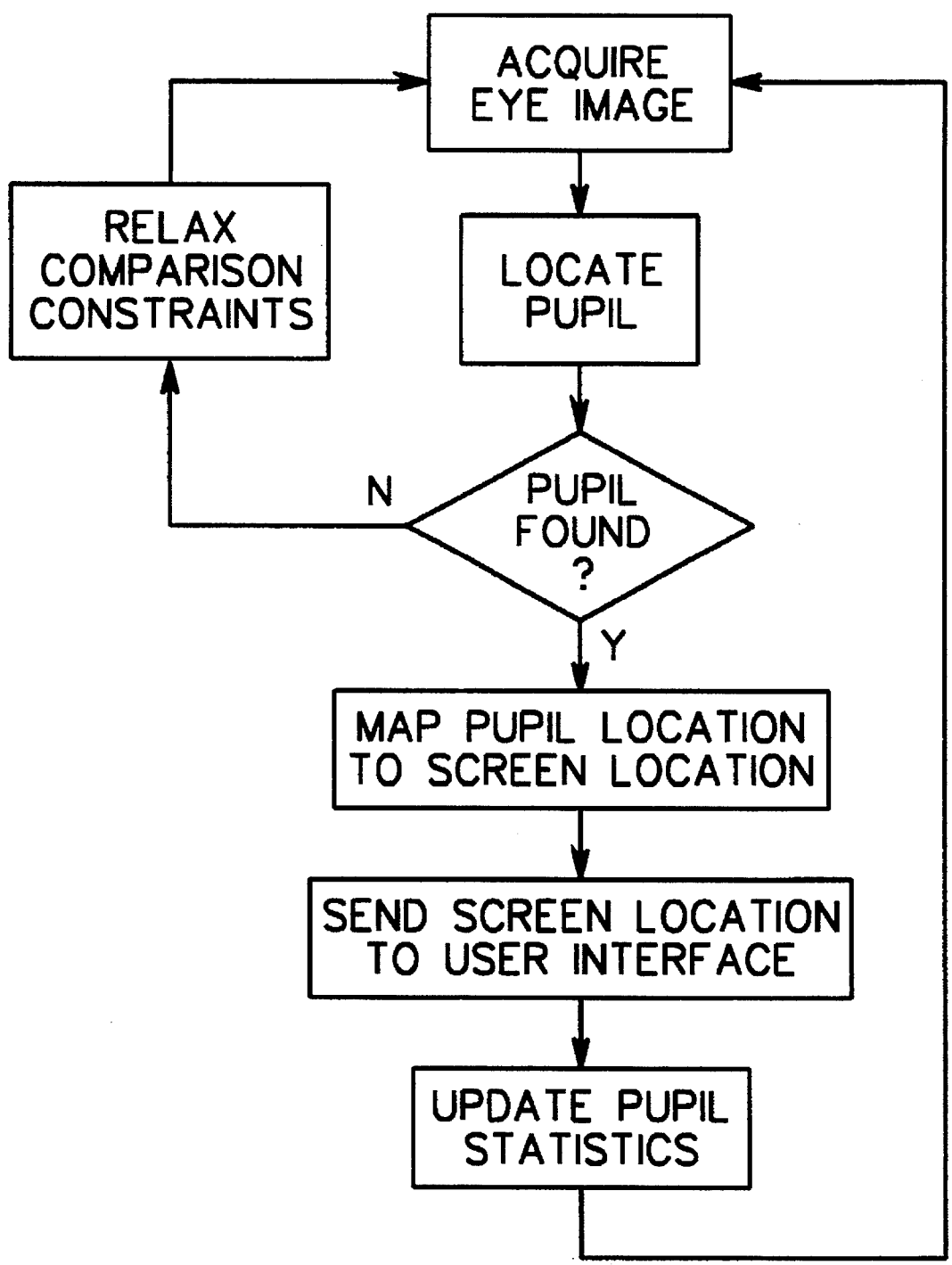
FIGS. 15–19 are flowcharts illustrating the operation of the vision-tracking system of the present invention.
Figure 16:
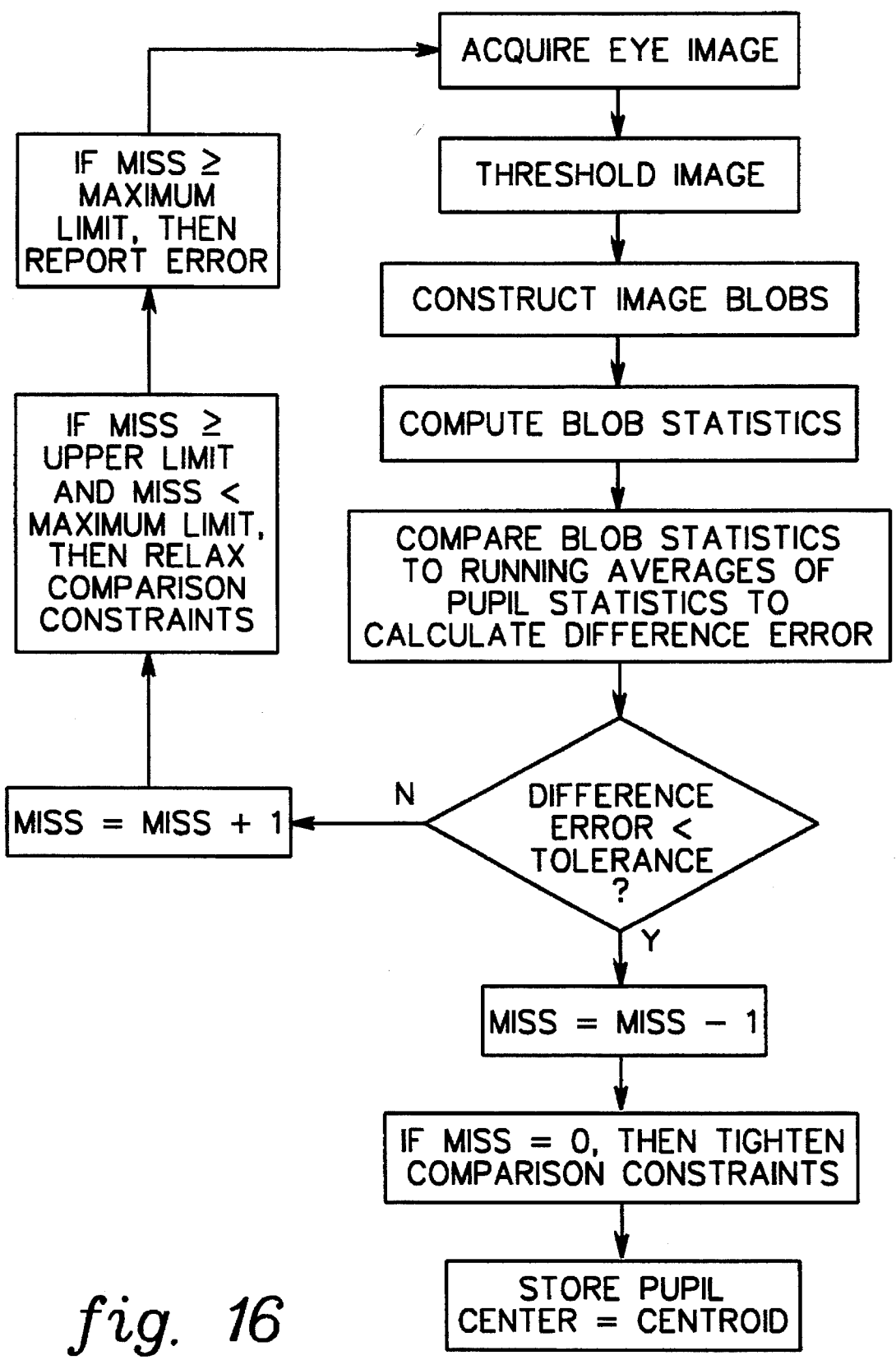
Figure 17:
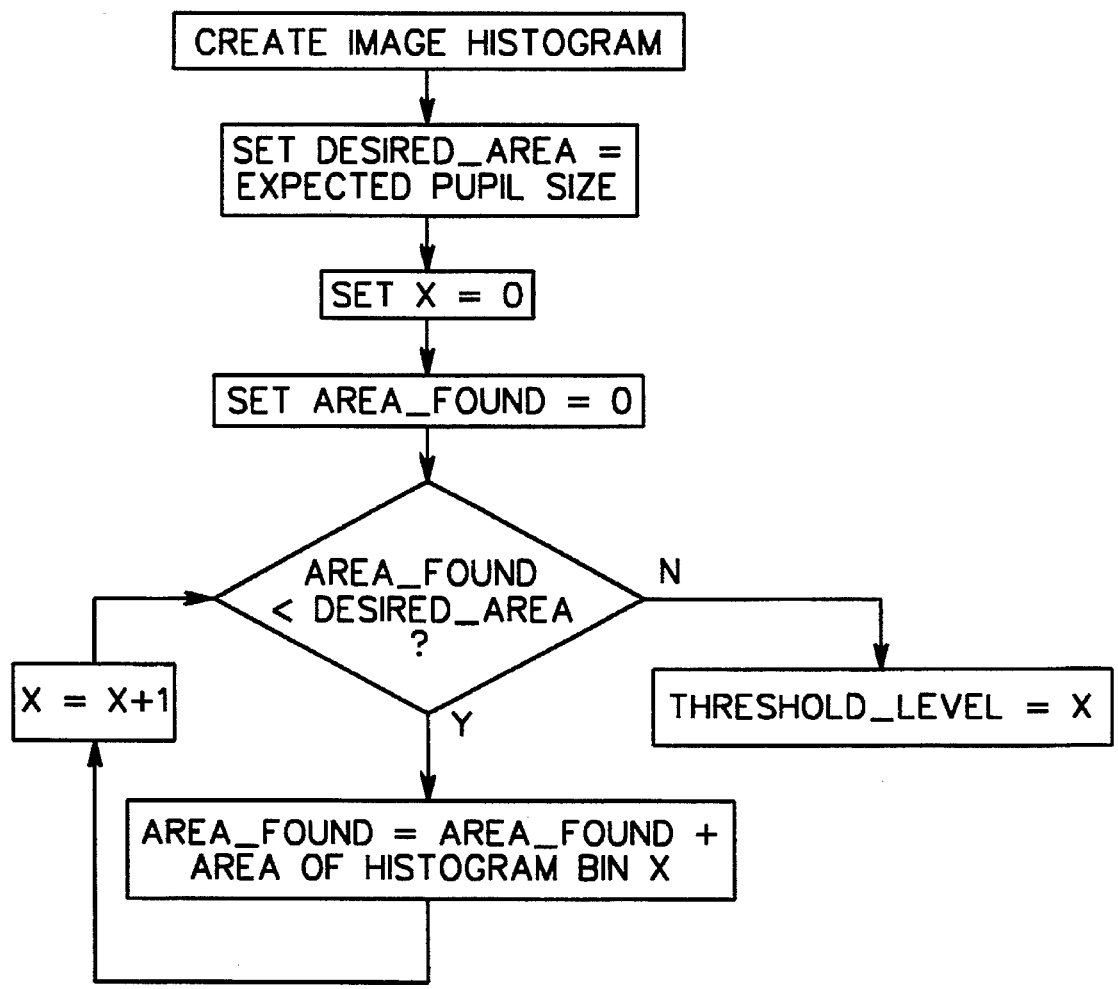

FIGS. 15–17 are flowcharts illustrating the operation of the vision-tracking system of the present invention. These flowcharts are generally self-explanatory, but some additional description is provided here. FIG. 15 shows the high-level method for determining the user's point of regard according to the present invention. Referring to FIG. 15, after an eye image is acquired, a procedure locates the pupil's position. If the pupil's centroid (in x,y image coordinates) has been located, then the pupil's location as determined in image coordinates is mapped into a corresponding location in screen coordinates (corresponding, for example, to the user's point of regard on a display screen). If the pupil is not found for the eye image frame currently being processed, then the comparison restraints are relaxed and another eye image is acquired and digitized for processing.

Once the pupil's screen location has been determined as above, the screen coordinates are sent to the user interface to provide feedback to the user. For example, these coordinates may be used to display a cursor on a display screen with the position of the cursor corresponding to the point of regard of the user's eye as determined by the eye-tracking system. As discussed above, after each successful pupil blob selection, the statistics for the user's pupil blob are updated.

FIG. 16 illustrates the pupil location process of FIG. 15 in greater detail and this process begins by accepting digitized pixel data for the eye image. Next, an image thresholding process, which is shown in greater detail in FIG. 17 and discussed below, returns an intensity threshold for the current pixel image. This threshold defines a binary image which is used to construct pixel image blobs as discussed above. Then, a counter MISS is initialized to zero, and blob statistics (for example, area and length-to-width ratio) are determined for each of the defined blobs. Each blob's statistics are compared to the respective running averages for previously-selected pupil blobs to determine a difference error. If this error is less than the pre-determined tolerance, say 10%, and MISS is greater than zero, then MISS is decremented by one. If MISS equals zero, then the comparison tolerances are tightened to their baseline values, as discussed above. The baseline tolerance values are, for example, a blob area within 10% of the running average blob area and an eccentricity within 5% of the running average blob eccentricity. If these tolerances are already at their baseline values, they are unchanged. The centroid for the selected pupil blob is then stored as the pupil's location in image coordinates. On the other hand, if the calculated difference error is not less than the percentage tolerance, then MISS is incremented by one. If MISS equals a pre-determined UPPER LIMIT, then the comparison constraints are relaxed as discussed above, and a new eye image is acquired.

In some cases the pupil location method fails to select a pupil blob because one or more of the blob statistics are not within the maximum tolerance limits. In these cases, it is unlikely that the pupil will be re-acquired by the eye-tracking system, and the pupil location method returns an error message to the system (this occurs when MISS is greater than or equal to a pre-determined value MAXIMUM LIMIT, which may have a value of say 8). A typical response to this error message would be recalibration of the system by the user.

FIG. 17 illustrates the image thresholding method according to the present invention. First, a histogram is created for the pixels in the current eye image, as discussed above. A constant "DESIRED_AREA" is set equal to the expected pupil size, an index counter X is set to zero, and a variable "AREA_FOUND" is set to zero. Counter X corresponds to the current bin of the histogram (e.g. 0<X<127 as in FIG. 5), and variable AREA_FOUND accumulates the total histogram area for all histograms traversed thus far in the current process. For the first histogram bin (X=0), if AREA_FOUND is less than DESIRED_AREA, then the pixel area of the first histogram bin is added to AREA_FOUND, and X is incremented by one to select the next histogram bin. Each consecutive histogram bin is traversed by incrementing X until AREA_FOUND is greater than or equal to DESIRED_AREA at which point the intensity threshold level is determined by the value of X.

Initially, DESIRED_AREA is set to an estimate of the expected pupil size. Alternatively, the pupil is observed by the system at start-up, and the area of the pupil is calculated and stored as DESIRED_AREA. However, once the system is in operation, DESIRED_AREA is preferably the running average area for previously selected pupil blobs.

As described in detail above, determining the point of regard of the eye on a display screen is a basic function of the eye-tracking system. However, although the description herein primarily refers to determining the eye's point of regard, the eye's line of sight is closely related to its point of regard, and other eye-tracking systems according to the present invention could alternatively determine the line of sight.

Some eye physiology related to the line of sight is briefly discussed here to help explain the relationship between point of regard and line of sight. The retina of the eye contains photosensitive cells which sense light entering the eye from the outside world, and the fovea is the part of the retina having cells with the highest visual acuity. Opposite the retina, the pupil is the round aperture in the iris of the eye through which light enters the eyeball. The line of sight of the human eye is a line intersecting both the fovea and the center of the pupil, and the point of regard of the eye is the point of intersection of the line of sight with an object in the real world, such as a video monitor. As will be recognized by one of skill in the art, the line of sight is related to the point of regard by a well-known vector transformation for an eye-tracking system in which the positions of the camera and display screen are fixed relative to the eye and to one another. The scope of the present invention is intended to cover systems that determine the line of sight of the eye rather than, or in addition to, the point of regard.

Alternative Image Processing Approach

In an alternative embodiment of the present invention, the image processing as described above may be altered so that the position of the user's pupil is determined relative to one or more radiation intensity highlights created by the IR LEDs or other light source used to illuminate the user's eye. In this alternative, the pupil's relative position (e.g. $X_{delta}$, $Y_{delta}$) in image coordinates is mapped into a point of regard in screen coordinate space. As will be discussed below, the aforementioned image processing is substantially unchanged in this alternative embodiment with the exception of the additional processing necessary to locate the radiation highlight(s).

In general, one of two or more radiation highlights is located and selected as a reference, and the pupil's centroid position is determined relative to this reference. More specifically, the eye-tracking system performs the following steps to determine the pupil's relative position:

selecting a second pixel intensity threshold, greater in intensity than the first pixel intensity threshold discussed previously, for the segmentation of the pixel data into third and fourth groups, the second pixel intensity threshold selected so that the total pixel area of the fourth group is substantially equal to a predetermined expected total image area corresponding to all highlights of the light sources illuminating the eye;

grouping individual pixels from the fourth group into a second set having at least one pixel blob;

selecting from the second set one of the pixel blobs corresponding to a first highlight image which corresponds to the first light source; and comparing the relative positions of the pixel blob corresponding to the pupil image and the pixel blob corresponding to the first highlight image to determine the point of regard of the eye.

The second pixel intensity threshold is selected so that the total pixel area above the second threshold in the pixel intensity histogram will be equal to the combined area of all highlights in the eye image. It is expected that the areas corresponding to the highlights in the eye image will consist of substantially all light pixels. Also, it should be noted that the second pixel intensity threshold is applied to the same pixel data as for the first pixel intensity threshold, but the light and dark groups (i.e. the third and fourth groups mentioned above) resulting from the application of the second intensity threshold to the pixel data are different from the light and dark sets resulting from the use of the first intensity threshold.

After segmenting the pixel data into light and dark sets based on the second threshold, the pixel data is processed to define blobs in a manner substantially similar as that described above for defining blobs consisting of dark pixels. Now, however, the blobs will consist of light pixels, and the goal of the image processing is to locate the one or more highlight blobs corresponding to the radiation highlights.

In the preferred embodiment, after these highlight blobs are located, only one of them is selected to use a reference for calculating the pupil's relative position. In one case, the leftmost highlight is always used (i.e. the highlight blob having the smallest X coordinate), but in other cases the rightmost or other highlight could be selected. It is only necessary that the same highlight (relative to any other highlights) be selected each time.

After selecting the leftmost highlight blob (having a position of $X_{highlight}$, $Y_{highlight}$) and the pupil blob (having a position of $X_{eye}$, $Y_{eye}$), the pupil's relative position is calculated. The pupil's relative position is defined as ($X_{delta}$, $Y_{delta}$) where $X_{delta}=X_{eye}-X_{highlight}$, and $Y_{delta}=Y_{eye}-Y_{highlight}$. After $X_{delta}$ and $Y_{delta}$ are determined, the remainder of the system's operation, such as mapping the image coordinates to screen coordinates, is substantially similar to that for the first embodiment discussed previously. In other words, $X_{delta}$ will substantially be used instead of $X_{eye}$, and $Y_{delta}$ instead of $Y_{eye}$.

Figure 18:
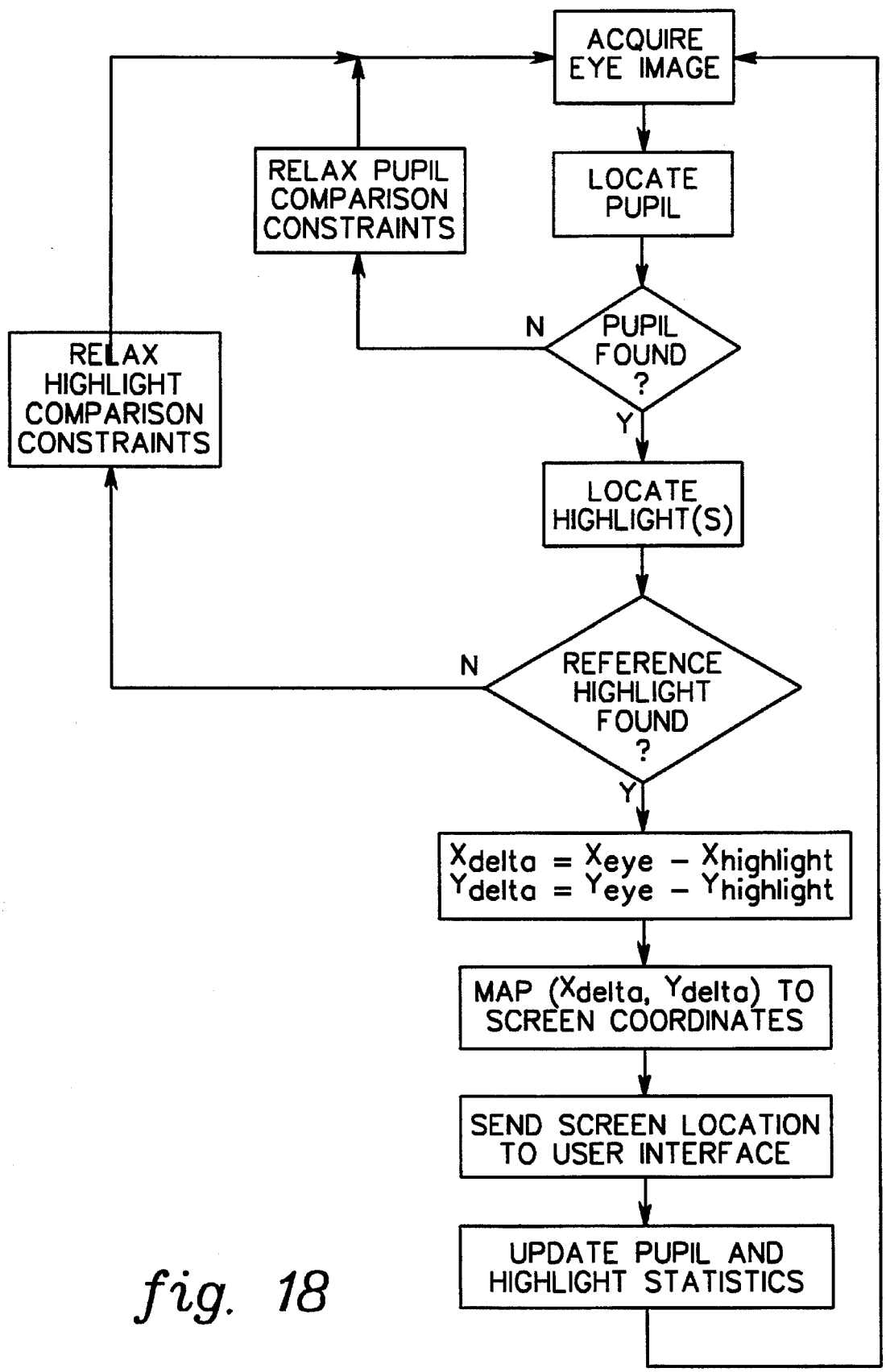

FIG. 18 is a flowchart further illustrating the processing method according to this alternative embodiment. The method presented in FIG. 18 is similar to that illustrated in FIG. 15 with a few exceptions. After the pupil centroid is located, the radiation highlights are located. The highlight location method is substantially similar to that used to locate the pupil except that blob comparisons are made using statistics expected for a highlight blob, such as its area and eccentricity, and the running averages used for these comparisons correspond to radiation highlights.

As for the pupil location loop, the comparison tolerances may be relaxed and tightened for the highlight location loop. This relaxation and tightening is substantially similar to that done for the pupil location method. Next, after the highlight blobs are defined and the reference highlight is selected, $X_{delta}$ and $Y_{delta}$ are calculated and used to determine the user's point of regard. Also, it should be noted that both the pupil and highlight statistics will be updated in this embodiment.

In other embodiments, rather than calculating the pupil's position relative to just one of the highlights, it may be desirable to calculate the pupil's position relative to, for example, left and right highlights (e.g. to determine an $X_{delta-left}$ and an $X_{delta-right}$). Here, for example, $X_{delta-left}=X_{eye}-X_{highlight-left}$, and a similar result would apply for the Y coordinate direction. Then, the function for mapping from image to screen space is determined in general as a function of $X_{delta-left}$, $X_{delta-right}$, $Y_{delta-left}$, and $Y_{delta-right}$. Examples of some mapping functions are discussed below.

System Calibration

Prior to acquiring eye image data with the camera to be used as control input to the system's computer, the eye-tracking system is calibrated to determine a mapping relationship between the relative position of the pupil's center and the point of regard on a display screen. This is called system calibration and is now discussed in detail below.

Figure 19:
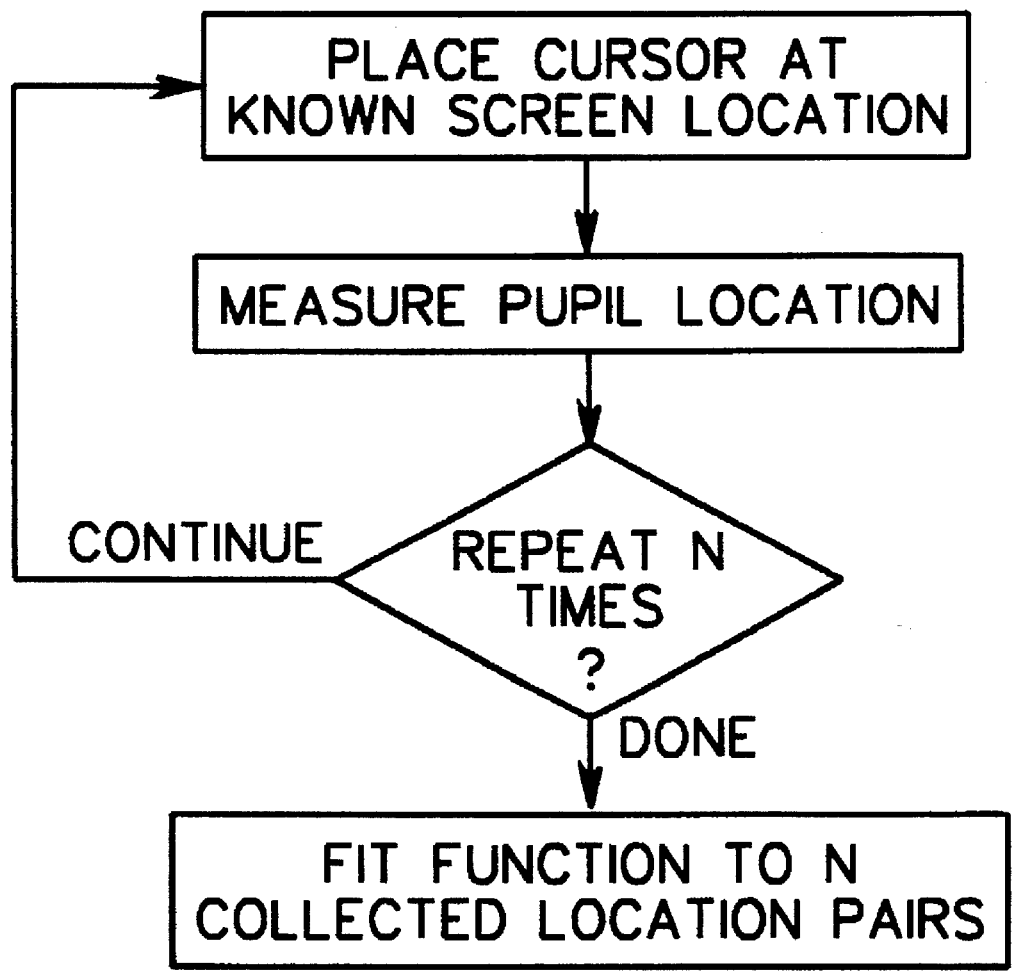

FIG. 19 illustrates a preferred calibration method for the eye-tracking system. By this method, a cursor is placed at a known location (this location is defined, for example, in screen coordinates $X_{screen}$, $Y_{screen}$) on the user interface, say a display screen, and the user then looks at this cursor for a set period of time. During this time the eye-tracking system determines the user's pupil location (this location is defined in image coordinates $X_{eye}$, $Y_{eye}$). This operation is then repeated N times. Following these N times, a set of screen coordinates with its corresponding set of image coordinates has been collected. Finally, in this preferred embodiment, polynomial functions are fitted to this data to develop mapping functions for a transformation from x and y image coordinates to x and y screen coordinates. Several data point image and screen coordinate pairs are acquired at each screen location to improve the optimization of the polynomial coefficients (e.g. by reducing the effects of spurious data points). The functions used are next described in greater detail below.

In the most general case, $X_{screen}$ is determined as a function of $X_{eye}$ and $Y_{eye}$, and $Y_{screen}$ is determined as a function of $X_{eye}$ and $Y_{eye}$. In a preferred approach, chosen to reduce the number of required calculations, the procedure used to find the mapping functions maps a least-squares polynomial function for the X and Y coordinates. Starting with matched pairs of data ($X_{eye}$, $Y_{eye}$), ($X_{screen}$, $Y_{screen}$), *in the preferred embodiment two third-order polynomial functions of the following form are generated:*

$$X'_{screen}=a_o+a_1X_{eye}+a_2X^2_{eye}+a_3X^3_{eye}$$

$$Y'_{screen}=b_o+b_1Y_{eye}+b_2Y^2_{eye}+b_3Y^3_{eye}$$

The fitting procedure minimizes the fitting error between the actual $X_{screen}$ data values and the $X'_{screen}$ value calculated from the corresponding actual $X_{eye}$ data value by optimizing the polynomial coefficients ($a_0$, $a_1$, $a_2$, $a_3$). Similarly, the fitting error is minimized between actual $Y_{screen}$ data and the $Y'_{screen}$ value calculated from actual $Y_{eye}$ data by optimizing coefficients ($b_0$, $b_1$, $b_2$, $b_3$). Although a third-order polynomial is described here, in other embodiments polyhomials of general order n (n=1,2 ... N) may be used.

Since the spatial relationships between the camera, display screen, and user's eye can change slightly each time the helmet or other mounting device is removed and replaced, it is preferable to re-perform this calibration at the start of each user's session. Also, although different users may use the eye-tracking system, measuring calibration data permits the relationship between pupil location and screen location to be readily established for each user.

One limitation on this calibration method is that the user's eye movements need to be substantially repeatable following calibration. One possible cause for a lack of repeatability in eye movements is movement of the camera, screen, or both relative to the user's eye after the calibration has been performed. Thus, the user helmet must fit substantially snug on the user's head to prevent this adverse movement.

Figure 20A:
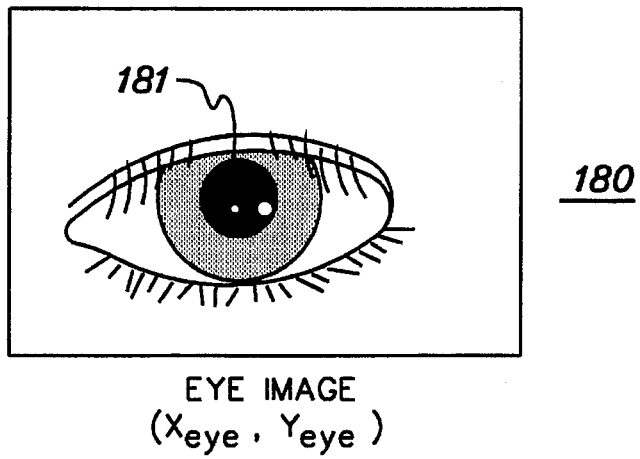
FIGS. 20a–20c illustrate the mapping of an image from image coordinate space to display screen coordinate space.
Figure 20B:
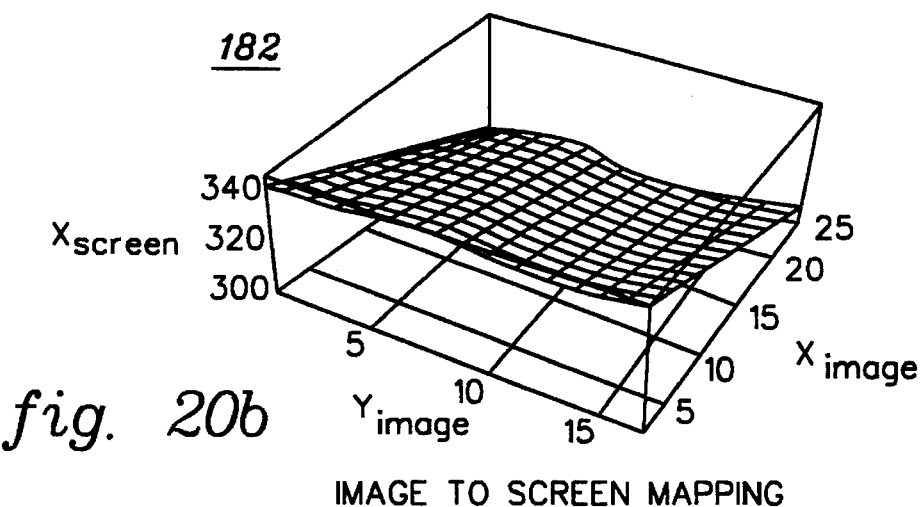
Figure 20C:
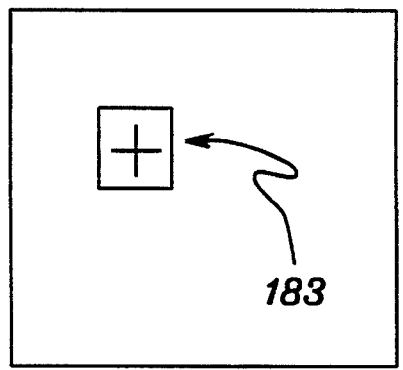

FIGS. 20a–20c are conceptual diagrams that illustrate a transformation from image coordinate space ($X_{eye}$, $Y_{eye}$) to display screen coordinate space ($X_{screen}$, $Y_{screen}$). A typical eye image 180 has a pupil 181 with a location defined in image coordinates ($X_{eye}$, $Y_{eye}$). The eye-tracking system uses a mapping 182 (only the mapping for $X_{screen}$ is shown) to determine the user's point of regard 183 (indicated as a grid box with a crosshair cursor therein) on a display screen 184 in screen coordinates ($X_{screen}$, $Y_{screen}$). Mapping 182 shows a generalized value for $X_{screen}$ as a function of a surface in ($X_{eye}$, $Y_{eye}$) image space. A generalized mapping for $Y_{screen}$ also exists, but is not shown.

Figure 21:
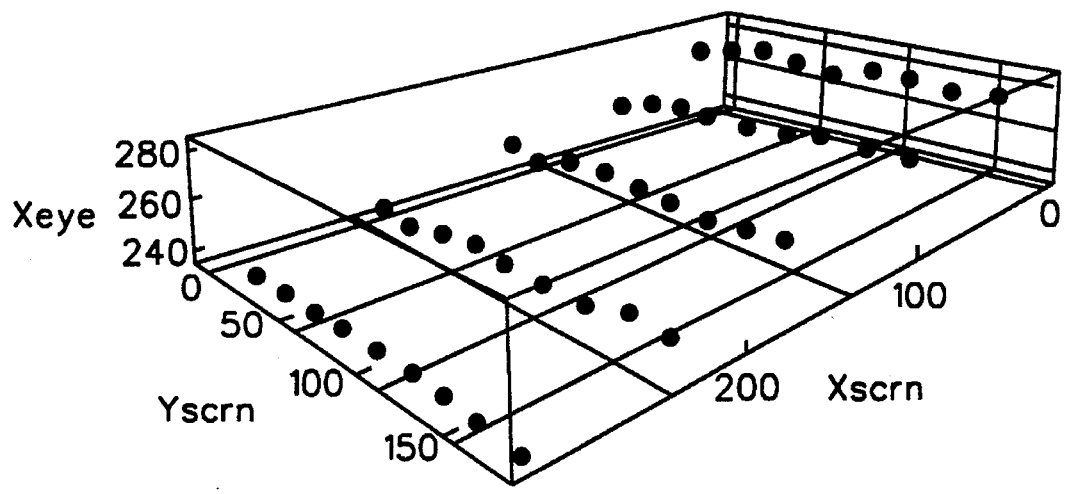
FIG. 21 illustrates the relationship between the x coordinate of the pupil in image coordinate space and the (x,y) coordinates in display screen coordinate space.
Figure 22:
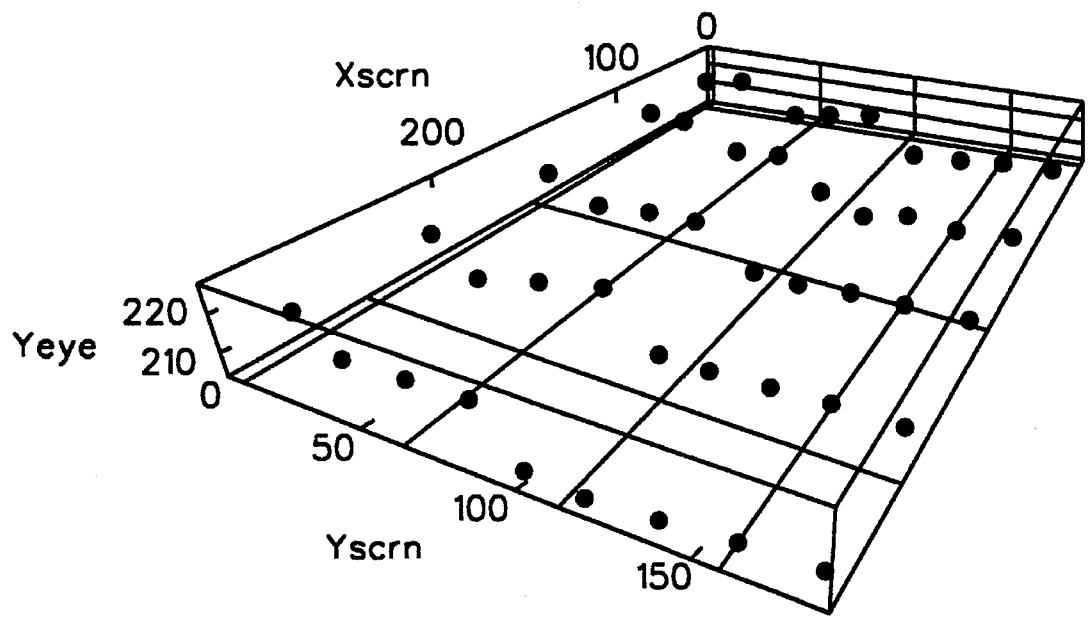
FIG. 22 illustrates the relationship between the y coordinate of the pupil in image coordinate space and the (x,y) coordinates in display screen coordinate space.

In one example of a calibration as described above, display screen 184 was divided into a 5×5 grid, and a grid box as shown in FIG. 20c was turned on successively in a left-to-right, top-to-bottom scan. At each grid location the position of the user's pupil was measured by the eye-tracking system. The measured pupil location and known screen location were stored for each grid location, with a total of five coordinate pairs collected for each grid location. FIGS. 21 and 22 illustrate the results of this example. FIG. 21 shows the relationship between the measured $X_{eye}$ position for the pupil and the corresponding screen location ($X_{screen}$, $Y_{screen}$). It should be noted that the relationship for $X_{eye}$ is substantially linear and appears to be substantially decoupled from the orthogonal screen direction, indicated by the $Y_{screen}$ coordinate. However, this result is for one particular user and is not necessarily universal. For other users or cases there may be a y-coordinate dependency that should be included in the calibration functions.

Similarly, FIG. 22 shows the relationship between the measured $Y_{eye}$ position and the corresponding screen location ($X_{screen}$, $Y_{screen}$). Here, the relationship for $Y_{eye}$ is not as linear as for $X_{eye}$ 12 above, but it does appear to be substantially decoupled from the orthogonal screen direction, indicated by the $X_{screen}$ coordinate.

In some cases the calibration will become invalid due to external factors that the system cannot compensate for. In such a case, an external switch input can be provided to permit the user to recalibrate the system if performance shifts or becomes unsatisfactory for some reason. This switch may be, for example, a head-motion-activated switch or breath-activated switch.

For the alternative image processing embodiment, the calibration method used is substantially identical to that described above. The mapping from ($X_{delta}$, $Y_{delta}$) to ($X_{screen}$, $Y_{screen}$) may be accomplished by collecting pairs of ($X_{delta}$, $Y_{delta}$), ($X_{screen}$, $Y_{screen}$) data and determining mapping functions as described above where $X_{delta}$ is used instead of $X_{eye}$, and $Y_{delta}$ is used instead of $Y_{eye}$. One difference from the above method, however, may be a dependence of $X_{delta}$ to both the X and Y directions, and likewise for $Y_{delta}$.

System Performance

The performance of the eye-tracking system is now discussed. One measure of performance is measurement accuracy in determining the point of regard. Specifically, this accuracy is defined as the deviation of calculated $X_{screen}$ values from the actual $X_{screen}$ value (for the known position of the user's point of regard). The smaller this deviation, the more reliably eye movements are transformed into their corresponding screen position.

Measurement accuracy was tested for one particular eye-tracking system by the following method. First, the system was calibrated for a given user, and then the cursor was moved to a series of different screen locations with the user voluntarily following the cursor's movement. At each screen location, the user's pupil location was measured and stored along with the corresponding screen location of the cursor (which was known). The measured pupil location was mapped into a calculated screen location for each cursor position on the screen. Finally, the calculated screen position was plotted versus the actual, known screen position.

Figure 23A:
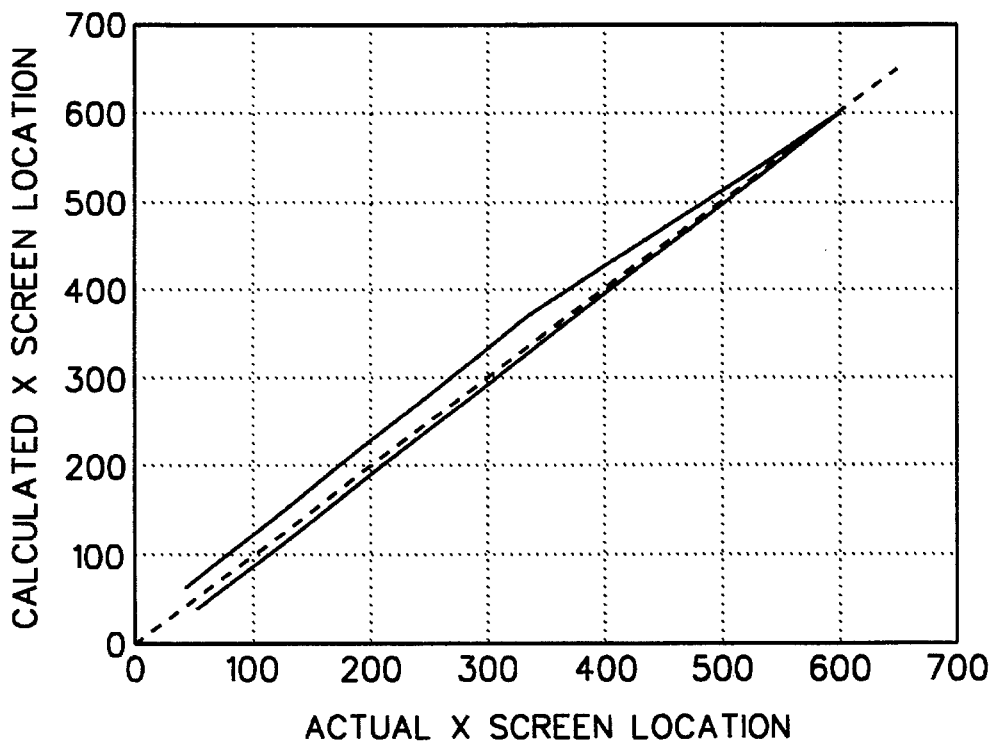
FIGS. 23a, 23b, 24a, and 24b are graphs illustrating calculated screen location versus actual screen location for both the x and y coordinates for two different test cases.
Figure 23B:
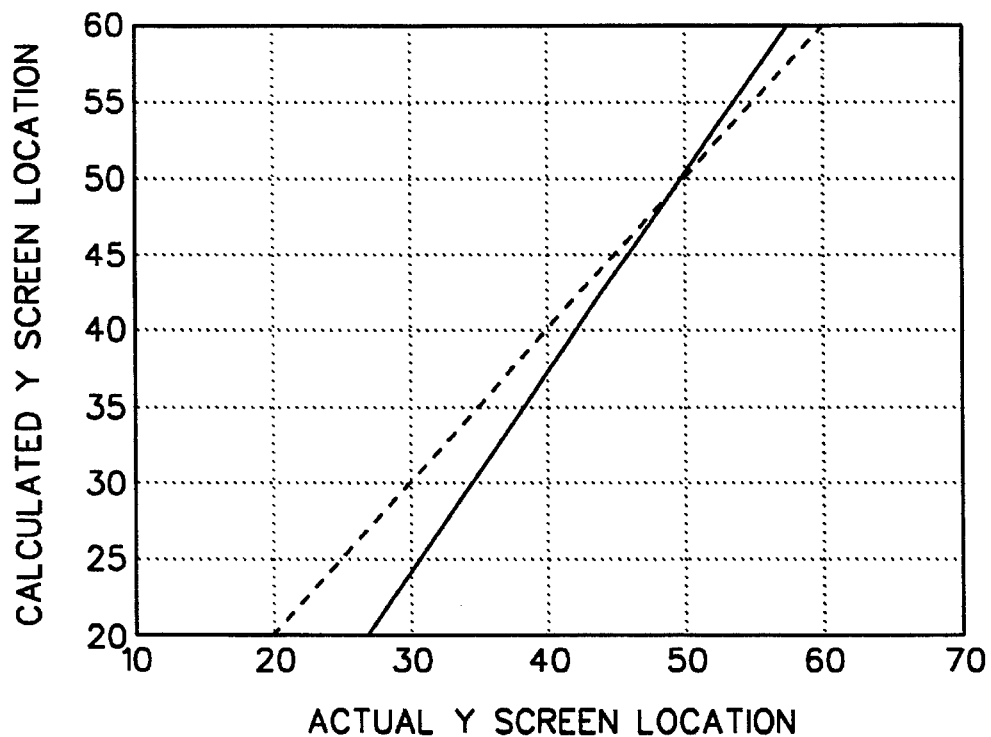

FIGS. 23a, 23b, 24a and 24b illustrate results from this testing for two different patterns of cursor movement on a screen having a size of 640×200 pixels. FIGS. 23a and 23b illustrate the results from a cursor pattern scanning left-to-right across the screen on two different horizontal lines. Each line was separated by 40 pixels in the Y direction. For an ideal system, calculated and actual locations are identical, and there is thus no deviation. This ideal response is indicated in the graphs as a dashed 45 degree line.

Figure 24A:
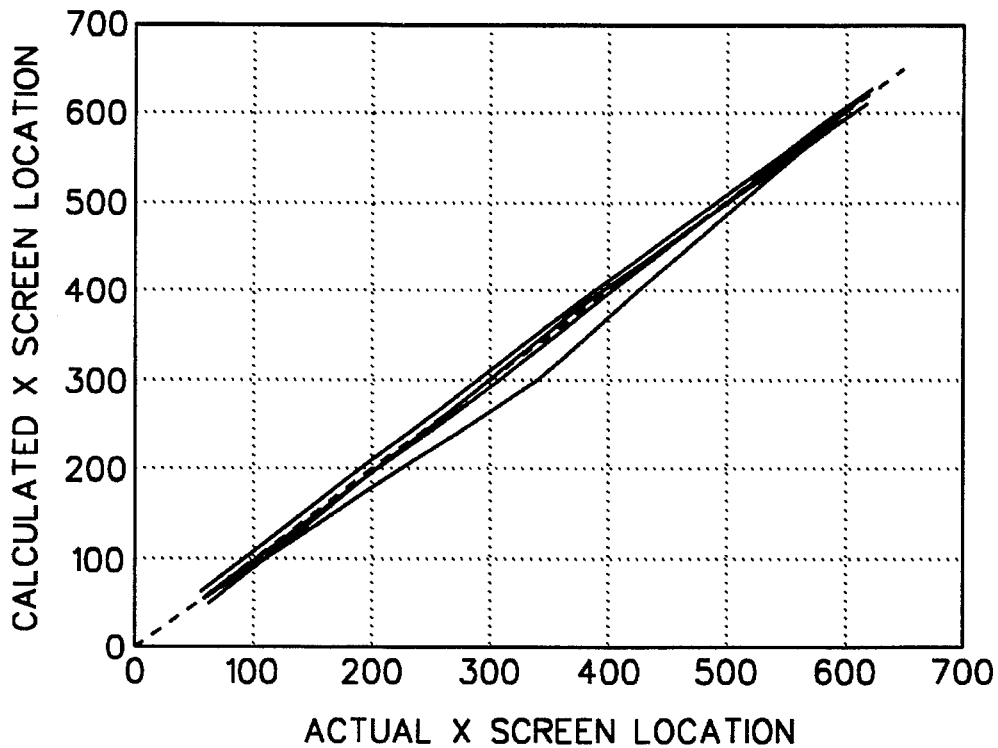
Figure 24B:
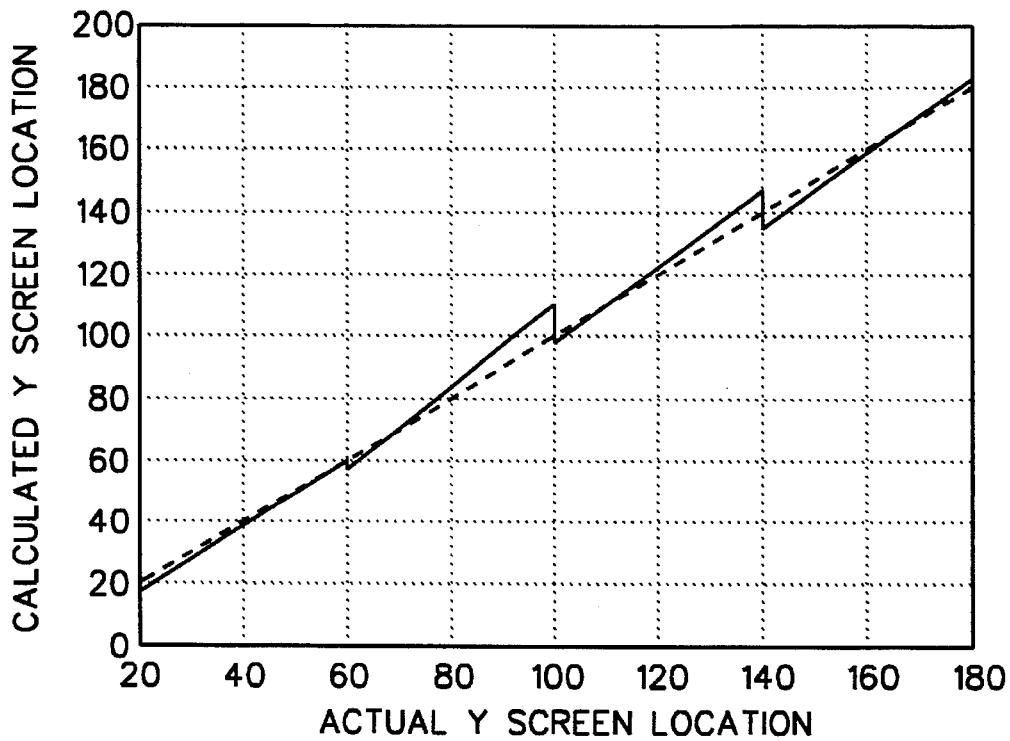

FIGS. 24a and 24b illustrate results where the pattern was extended to four different horizontal scan lines (i.e. the screen was divided into a 4×4 grid with 40 pixels between grid locations). In FIG. 24b, the jumps between different horizontal scan lines appear as discontinuities.

Another measure of performance is the system's speed of response. One specific prototype system, implemented with a 640×480 pixel image and using a Sun SPARCstation2 computer, has an update rate of about 1.5 seconds (i.e. the most recent eye position is indicated by a cursor that is updated every 1.5 sec.). However, an even faster update rate would be more desirable, such as a rate of four updates per second. One way to increase system speed is in the selection of the frame grabber card used for analog-to-digital conversion of the eye image.

In particular, there are several desirable characteristics for the frame grabber card used in the system. First, it is desirable that the frame grabber allow the host computer to access the on-board memory on the card directly, and begin the capture of a second image while processing the current image. Also, it is preferable that the frame grabber card contain look-up tables (LUTs) for requantizing the pixels captured. LUTs permit the frame grabber to perform image thresholding in hardware at the card's frame rate throughput, rather than in software on the host computer.

Further speed increases can also be achieved in some cases by altering the blob definition method. As described above, blob definition operates on the entire pixel image. However, by limiting examination, and thus blob definition, to only a portion of the full pixel image (say, a 320×240 or 220×160 pixel subset), system speed can be increased significantly. The pupil typically only occupies about 10% of the total video image. By keeping a running average of the centroid location for previously-selected pupil blobs, an active image region can be examined that is centered about the running average centroid location.

In some cases the use of a smaller active image region will result in a failure to select the pupil blob. In these cases, in a manner similar to that described above for percentage comparison tolerances, the size of the active window can be incrementally increased until the pupil blob is again successfully selected. Then, the active window size can be reduced to its baseline size, say 220×160 pixels.

In addition, modifications can be made to the image thresholding method to increase speed. For example, if it can be assumed that the eye images will not vary significantly from frame to frame, then the histogram from a prior frame can be used to set the threshold value for the current frame. When the entire image needs to be scanned for an additional operation, like locating the pupil blob, the histogram for the current image can be constructed.

System User Interface

In general, there are a multitude of possible user interfaces which can be implemented using the present invention. One of skill in the art will recognize the modifications required to these particular interfaces in order to implement the present invention.

As just one example of a possible user screen interface, a grid of boxes is provided on the display screen in the form of a menu. Each box can be associated with a link to a different screen, a command, or a message. A command box will control the functioning of the system. An example of such a command box would be one for exiting the user program. Another type of box would be a message box. This would be a more generic box and would represent information that could be sent to an external system or cause the initiation of a different task on the same system. For example, an external speech synthesizer may be attached to the serial port of the system computer. A message could then be sent to the serial port instructing the speech synthesizer to produce a specific word. This message, along with information instructing the computer where to direct this message, would be stored in a message box.

ADVANTAGES OF THE PRESENT INVENTION

An advantage of the present invention is that the image processing method can be implemented to require only a single pass of each image frame. This reduces the computational load on the system relative to prior systems so that the system's efficiency is improved and its cost decreased. Another advantage is that changing lighting conditions are accommodated through the adjustment of the pixel intensity threshold for each image frame (recall, however, that the expected pupil size area criterion remains constant).

Another advantage of the eye-tracking system according to the present invention is that all components necessary to operate the system may be carried on the user's person, including a portable power supply. One skilled in the art will recognize that such a portable system may be built from the description provided herein. This portability provides flexibility in performing work that requires moving from one location to another during the work. The portability of the system permits a user to move his head relatively freely and to move around his environment without limitation. For example, a handicapped person can move around in a wheelchair without being restrained to a particular location by the eye-tracking system.

Although the present invention has been described in detail above, it is not intended to be limited to the specific form set forth herein, but, on the contrary, it is intended to cover such alternatives and equivalents as can reasonably be included within the spirit and scope of the invention as defined by the appended claims.

We claim:

1. A system for determining a point of regard, said system comprising:

camera means for acquiring a video image of a first vision means, said first vision means comprising a pupil, a position of said pupil corresponding to said point of regard, and said video image comprising a pupil image;

frame grabber means, coupled to said camera means, for accepting video data corresponding to said video image from said camera means and converting said video data to digital pixel data of a given dynamic range so as to provide said digital pixel data as a grayscale mapping of the video image;

computer means, coupled to said frame grabber means, for processing said digital pixel data to substantially determine the position of said pupil wherein said computer means includes:

memory means for providing an expected area value for the area of said pupil within said video image;

means for determining a grayscale threshold value in accordance with said expected area value and grayscale distribution of said digital pixel data;

means for segregating said digital pixel data into two separate binary groups as first and second groups using said grayscale threshold value as a discriminator; and means for substantially determining the position of said pupil in accordance with the segregated data;

feedback means, coupled to said computer means, for accepting data corresponding to the determined position of said pupil from said computer means and feeding back to said first vision means feedback information representative of the determined position; and support means, connected to said camera means and said feedback means, for fixing the relative physical positions of said camera means and said feedback means.

2. The system of claim 1 wherein said determining means of said computer means further comprises:

means for grouping contiguously related individual pixels from one of said first group or said second group into a first set of representative pixel blobs; and means for selecting from said first set of pixel blobs a pixel blob corresponding to said pupil image.

3. The system of claim 2 wherein said feedback means is a display screen; and said computer means further comprises:

means for determining the position of said pupil image in an image coordinate space; and means for mapping the position of said pupil image in the image coordinate space into a position in a display screen coordinate space.

4. System of claim 3 further comprising a calibration means for determining a mapping function between the image coordinate space and the display screen coordinate space, said calibration means comprising:

means for placing a cursor at a pre-determined position on said display screen;

means for orienting said point of regard to substantially coincide with said pre-determined position;

means for determining the position of the pupil image of said vision means in the image coordinate space;

means for repeating said steps of placing a cursor, orienting said point of regard, and determining the pupil image position a plurality of times to generate a plurality of cursor position-pupil image position data pairs; and means for fitting a curve to said data pairs to determine said mapping function.

5. The system of claim 3 wherein said position of said pupil image in image coordinate space is determined based on the centroid of said pixel blob selected as corresponding to said pupil image.

6. The system of claim 3 wherein said support means substantially fixes the relative physical position of said vision means relative to said camera and display screen.

7. The system of claim 2 wherein said computer means in selecting said pixel blob corresponding to said pupil image further comprises:

means for calculating a statistic for each pixel blob of said first set;

means for comparing said statistic of each pixel blob with an expected value corresponding to said pupil image to calculate a difference error; and means for selecting said pixel blob corresponding to said pupil image where said difference error is less than a pre-determined tolerance.

8. The system of claim 7 wherein the computer means further comprises:

a counter that is incremented after each failure to select a pixel blob corresponding to said pupil image for the current video image being processed by said computer means; and adjustment means for relaxing said tolerance by a pre-determined quantity after said counter reaches a pre-determined upper limit.

9. The system of claim 8 wherein:

said counter is decremented after each successful selection of a pixel blob corresponding to said pupil image for the current video image being processed by said computer means; and said adjustment means tightens said tolerance to a pre-determined baseline value after said counter reaches a pre-determined lower limit.

10. The system of claim 7 wherein said statistic for each blob is an area, length-to-width ratio, or a centroid.

11. The system of claim 7 wherein said expected value corresponding to said pupil image is a running average of a plurality of statistics calculated for previously-selected pixel blobs corresponding to pupil images for previous video images.

12. The system of claim 2 further comprising at least one light source mounted on said support means, each light source illuminating said vision means and creating an associated radiation intensity highlight on said vision means.

13. The system of claim 12 wherein said computer means in processing said digital pixel data further comprises:

means for selecting a second pixel intensity threshold, greater in intensity than said grayscale threshold value, for the segmentation of said pixel data into third and fourth groups, said second pixel intensity threshold selected so that the total pixel area of said fourth group is substantially equal to a pre-determined expected area for all highlights of said light sources illuminating said vision means;

means for grouping contiguously related individual pixels from said fourth group into a second set of respective pixel blobs;

means for selecting from said second set of pixel blobs a pixel blob corresponding to a first highlight; and means for comparing the relative positions of said pixel blob corresponding to said pupil image and said pixel blob corresponding to said first highlight to determine said point of regard.

14. The system of claim 13 wherein said feedback means is a display screen and said computer means in processing said pixel data further comprises:

means for determining the relative position of said pupil image relative to said first highlight in an image coordinate space; and means for mapping said relative position of said pupil image in the image coordinate space into a point of regard in a display screen coordinate space.

15. The system of claim 14 further comprising a second light source mounted on said support means, said second light source illuminating said vision means and creating a second radiation intensity highlight on said vision means.

16. The system of claim 15 wherein the position of said pupil image relative to said second highlight is determined by said computer means.

17. The system of claim 1 wherein said computer means processes data corresponding to a plurality of video images to substantially determine the position of said pupil.

18. An eye-tracking system for determining a point of regard on a display, said eye-tracking system comprising:

a display screen providing said display and displaying information corresponding to said point of regard;

a camera for acquiring a video image of an eye having a pupil, the position of said pupil corresponding to said point of regard, and said video image comprising a pupil image;

a frame grabber, coupled to said camera, for accepting video data corresponding to said video image from said camera and converting said video data to digital pixel data of a given dynamic range so as to provide said digital pixel data as a grayscale mapping of said video image;

a computer, coupled between said frame grabber and said display screen, for processing said digital pixel data to substantially determine said point of regard on said display screen wherein said computer includes:

memory means for providing an expected area value for the area of said pupil within said video image;

means for determining a grayscale threshold value in accordance with said expected area value and grayscale distribution of said digital pixel data;

means for segregating said digital pixel data into two separate binary groups as first and second groups using said grayscale threshold value as a discriminator; and means for substantially determining the position of said pupil in accordance with the segregated data; and a support, connected to said camera and said display screen, for substantially fixing the physical positions of said camera means and said display screen relative to said eye.

19. The eye-tracking system of claim 18 wherein said computer in processing said digital pixel data further comprises:

means for grouping contiguously related pixels from said first group into a first set of respective pixel blobs;

means for selecting from said first set a pixel blob corresponding to said pupil image;

means for determining the position of said pupil image by a calculated value based on a property of said selected pixel blob; and means for mapping the position of said pupil image in an image coordinate space into a position in a display screen coordinate space.

20. The eye-tracking system of claim 19 wherein said computer means in selecting the pixel blob from said first set further comprises:

means for calculating a statistic for each pixel blob in said first set;

means for comparing said statistic for each pixel blob in said first set with an expected value corresponding to said pupil image to calculate a difference error; and means for selecting from said first set the pixel blob corresponding to said pupil image where said difference error is less than a pre-determined tolerance.

21. The eye-tracking system of claim 20 further comprising at least a first light source mounted on said support, said first light source illuminating said eye and creating a radiation intensity highlight on the corneal surface of said eye.

22. The eye-tracking system of claim 21 wherein said computer in processing said digital pixel data further comprises:

means for selecting a second pixel intensity threshold, greater in intensity than said grayscale threshold valve, for the segmentation of said pixel data into third and fourth groups, said second pixel intensity threshold selected so that the total pixel area of said fourth group is substantially equal to a pre-determined expected total image area corresponding to the highlight of said first light source illuminating said eye;

means for grouping contiguously related individual pixels from said fourth group into a second set of respective pixel blobs;

means for selecting from said second set a pixel blob corresponding to a first highlight image of said first light source; and means for comparing the relative positions of said pixel blob corresponding to said pupil image and said pixel blob corresponding to said first highlight image to determine said point of regard.

23. The system of claim 22 wherein said computer in processing said digital pixel data further comprises:

means for determining the relative position of said pupil image relative to said first highlight image in the image coordinate space; and means for mapping said relative position of said pupil image in the image coordinate space into a point of regard in the display screen coordinate space.

24. The system of claim 23 further comprising a second light source mounted on said support means, said second light source illuminating said eye and creating a second radiation intensity highlight on said eye, wherein the position of said pupil image relative to a second highlight image corresponding to said second light source is determined by said computer.

25. The system of claim 22 wherein said first light source is a light-emitting diode.

26. The system of claim 22 further comprising a speech synthesizer coupled to said computer.

27. The system of claim 20 wherein all components of said system including a power supply can be carried on one's person.

28. The system of claim 20 wherein said camera and said display screen are both directed to the same eye.

29. In a vision-tracking system, a tracking method for determining a point of regard, said method comprising the steps of:

acquiring video data from a camera corresponding to a video image of a vision means, said vision means comprising a pupil, the position of said pupil corresponding to said point of regard, and said video image comprising a pupil image;

converting said video data to digital pixel data corresponding to said video image using an analog-to-digital interface coupled to said camera so as to provide said digital pixel data of a given dynamic range as a grayscale mapping of said video image;

providing an expected area value for said pupil;

determining a grayscale threshold value in accordance with said expected area value and grayscale distribution of said digital pixel data;

segregating said digital pixel data into first and second groups using said grayscale threshold value as a discriminator;

determining the position of said pupil in accordance with the segregated data of one of said first group or said second group; and providing feedback data corresponding to said pupil position from said computer.

30. The tracking method of claim 29 wherein said step of processing said pixel data further comprises the step of grouping contiguously related individual pixels from one of said first group or said second group into a set of respective pixel blobs.

31. The tracking method of claim 30 wherein said step of processing said pixel data further comprises the step of selecting one of said pixel blobs corresponding to said pupil image.

32. The tracking method of claim 29 wherein said step of providing feedback uses a display.

33. The tracking method of claim 32 further comprising the step of mounting said camera and said display, prior to said step of acquiring video data, to fix the relative physical positions of said camera and said display.

34. The tracking method of claim 29 wherein said feedback data is provided by a display screen, said grayscale threshold value is selected so that the total pixel area of said first group is substantially equal to a pre-determined expected pupil area, and said processing by said computer further comprises the steps of:

grouping contiguously related pixels from said first group into a first set of respective pixel blobs;

selecting from said first set a pixel blob corresponding to said pupil image;

determining the position of said pupil image by a calculated value based on a property of said pixel blob as selected; and mapping the position of said pupil image in an image coordinate space into a position in a display screen coordinate space.

35. The tracking method of claim 34 wherein said step of selecting the pixel blob from said first set comprises the steps of:

calculating a statistic for each pixel blob in said first set;

comparing said statistic for each pixel blob in said first set with an expected value corresponding to said pupil image to calculate a difference error; and selecting from said first set the pixel blob corresponding to said pupil image where said difference error is less than a pre-determined tolerance.

* * * * *